United States Patent
Ranoa et al.

(10) Patent No.: US 11,530,457 B2
(45) Date of Patent: Dec. 20, 2022

(54) SALIVA-BASED MOLECULAR TESTING FOR SARS-COV-2

(71) Applicant: The Board of Trustees of the University of Illinois, Urbana, IL (US)

(72) Inventors: Diana Rose Ranoa, Champaign, IL (US); Robin L. Holland, Urbana, IL (US); Fadi G. Alnaji, Urbana, IL (US); Kelsie J. Green, Champaign, IL (US); Leyi Wang, Mahomet, IL (US); Christopher B. Brooke, Champaign, IL (US); Martin D. Burke, Champaign, IL (US); Timothy M. Fan, Mahomet, IL (US); Paul J. Hergenrother, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 17/636,469

(22) PCT Filed: Jun. 17, 2021

(86) PCT No.: PCT/US2021/037852
§ 371 (c)(1),
(2) Date: Feb. 18, 2022

(87) PCT Pub. No.: WO2021/257844
PCT Pub. Date: Dec. 23, 2021

(65) Prior Publication Data
US 2022/0275464 A1    Sep. 1, 2022

Related U.S. Application Data

(60) Provisional application No. 63/085,551, filed on Sep. 30, 2020, provisional application No. 63/040,612, filed on Jun. 18, 2020.

(51) Int. Cl.
*C12N 15/10* (2006.01)
*C12Q 1/70* (2006.01)

(52) U.S. Cl.
CPC ....... *C12Q 1/701* (2013.01); *C12Q 2600/158* (2013.01)

(58) Field of Classification Search
None
See application file for complete search history.

(56) References Cited

U.S. PATENT DOCUMENTS

| 10,000,795 B2 | 6/2018 | Birnboim et al. |
| 2002/0123038 A1 | 9/2002 | Taya et al. |
| 2020/0347465 A1 | 11/2020 | Schmidt et al. |
| 2021/0003528 A1 | 1/2021 | Esquivel-Upshaw et al. |
| 2021/0040571 A1 | 2/2021 | Lambie et al. |
| 2021/0108259 A1 | 4/2021 | Kidd et al. |
| 2021/0130886 A1 | 5/2021 | Bouchard et al. |

FOREIGN PATENT DOCUMENTS

| CN | 105917235 A | 8/2016 |
| WO | 2009021131 A2 | 2/2009 |
| WO | 2015035260 A1 | 3/2015 |

OTHER PUBLICATIONS

Fomsgaard et al., Euro Survell vol. 25, pp. 1-4 (Year: 2020).*
Srivatsan et al. (Bioxiv Apr. 23, 2020, pp. 1-11 (Year: 2020).*
Hank's Balanced Salt Solution (Year: 2022).*
Copan Universal Transport Medium (Year: 2022).*
Batejat et al., "Heat inactivation of the Severe Acute Respiratory Syndrome Coronavirus 2," bioRxiv, May 2020, 5pgs.
Fomsgaard et al., "An Alternative Workflow for Molecular Detection of SARS-CoV-2—Escape From the NA Extraction Kit-Shortage," Eurosurveillance, 25(14):1-4, Apr. 2020.
Hockmeyer et al., "Blueprint for a Pop-up SARS-CoV-2 Testing Lab," Nature Biotech., 38:791-797, Jun. 2020.
International Search Report and Written Opinion of the ISA/US in PCT/US2021/037852, dated Oct. 13, 2021, 10pgs.
Pastorino et al., "Evaluation of Heating and Chemical Protocols for Inactivating SARS-CoV-2," bioRxiv, Apr. 2020, 9pgs.
Ranoa et al., "Saliva-Based Molecular Testing for SARS-CoV-2 that Bypasses RNA Extraction," bioRxiv, Cold Spring Harbor Laboratory Press, pp. 1-35, Jun. 2020.
Srivatsan et al., "Preliminary Support for a "Dry Swab, Extraction Free" Protocol for SARS-CoV-2 Testing via RT-qPCR," bioRxiv, Apr. 2020, 11 pgs.
To et al., "Temporal Profiles of Viral Load in Posterior Oropharyngeal Saliva Samples and Serum Antibody Responses During Infection by SARS-CoV-2: An Observational Cohort Study," Lancet Infect Dis., 20(5):565-574, Mar. 2020.

(Continued)

*Primary Examiner* — Shanon A. Foley
*Assistant Examiner* — Myron G Hill
(74) *Attorney, Agent, or Firm* — Haukaas Fortius PLLC; Michael Haukaas

(57) ABSTRACT

A saliva-based testing method that bypasses the need for RNA isolation/purification is described herein. In experiments with inactivated SARS-CoV-2 virus spiked into saliva, this method has a limit of detection of 500-1000 viral particles per mL, rivalling the standard NP swab method. Initial studies showed excellent performance with 100 clinical samples. This saliva-based process is operationally simple, utilizes readily available materials, and can be easily implemented by existing testing sites thus allowing for high-throughput, rapid, and repeat testing of large populations.

4 Claims, 24 Drawing Sheets

(56) References Cited

OTHER PUBLICATIONS

Winichakoon et al., "Negative Nasopharyngeal and Oropharyngeal Swabs Do Not Rule Out COVID-19," J. Clin Microbiol., 58(5):e00297-20, May 2020.

Wu et al., "Coronavirus Disease 2019 Test Results After Clinical Recovery and Hospital Discharge Among Patients in China," JAMA Netw Open, 3(5):e209759, May 2020.

Wyllie et al., "Saliva Is More Sensitive for SARS-CoV-2 Detection in COVID-19 Patients Than Nasopharyngeal Swabs," N Engl J Med., 383:1283-1286, Sep. 2020.

* cited by examiner

A) Standard method:

*Laborious & supply chain bottlenecks*

NP swab & VTM ➡ RNA purification kit ➡ RT-qPCR

B) Saliva (EUA approval April 2020):

Saliva collection ➡ RNA purification kit ➡ RT-qPCR

C) Skipping RNA isolation (demonstrated in several publications):

NP swab & VTM ➡ RT-qPCR

D) UIUC Testing protocol:

Saliva collection ➡ RT-qPCR

E)

F)

SALIVA-BASED MOLECULAR TESTING FOR SARS-COV-2

RELATED APPLICATIONS

This application is a National Stage filing under 35 U.S.C. § 371 of International Application No. PCT/US2021/037852 filed Jun. 17, 2021, which claims priority under 35 U.S.C. § 119(e) to U.S. Provisional Patent Application Nos. 63/040,612 filed Jun. 18, 2020, and 63/085,551 filed Sep. 30, 2020, which applications are incorporated herein by reference in their entirety.

BACKGROUND OF THE INVENTION

The slow roll-out and inconsistent availability of diagnostic testing for SARS-CoV-2 has hobbled efforts to control the COVID-19 pandemic in many countries. Testing protocols based on the use of nasopharyngeal (NP) swabs as the collection agent, placed in a tube containing viral transport media (VTM), followed by RNA isolation/purification and subsequent analysis by RT-qPCR is currently the most common method (FIG. 1A). While some variant of this process has been implemented worldwide, there are multiple challenges with this workflow. Sample collection using NP swabs requires healthcare workers wearing personal protective equipment (PPE) to collect samples, the swabs can be uncomfortable for the patients during collection, and the swabs and the associated VTM have been in short supply at many times and in most locations. In addition, RNA isolation/purification is another significant bottleneck, both in the time and labor required for this process, and in the availability of the equipment and reagents. All these components also add to the cost of the testing process.

There is emerging consensus that widespread, frequently repeated testing is necessary for a safer return to activities that are important for society. Given the data suggesting that SARS-CoV-2 can be spread by pre-symptomatic/asymptomatic carriers, localized outbreaks could be dramatically reduced or prevented if individuals shedding SARS-CoV-2 could be readily identified and isolated. For example, imagine a testing bubble placed over a group that desires face-to-face interaction—employees of a company, members of a sports team, extended family networks, etc. If all members of the group could be tested for SARS-CoV-2, then isolated, then tested again after an appropriate time increment (likely ~4-5 days, in line with the incubation period for SARS-CoV-2), two negative tests would provide confidence for a safer return to activities. Of course, in practice there are challenges with total self-isolation and avoidance of others outside the testing bubble, but the above scenario represents one promising path forward, allowing positive cases to be identified and contained, and reducing the probability that pre-symptomatic/asymptomatic virus shedders unknowingly transmit SARS-CoV-2 to others. Unfortunately, as the size of a group grows larger, widespread, and frequent testing for SARS-CoV-2 using the standard testing protocol depicted in FIG. 1A becomes impractical. For example, it would be untenable to repeatedly test all members of a university in a short time period using this process.

When considering various sample collection possibilities, saliva is attractive due to the known detection of SARS-CoV-2 through oral shedding, and the potential for rapid and easy self-collection, thus minimizing the need for direct healthcare provider-patient contact and consequent conservation of personal protective equipment (PPE). In addition, a number of recent reports have detailed the detection of SARS-CoV-2 in saliva through the workflow in FIG. 1B, including a report showing higher viral loads in saliva when compared to matched NP swabs from the same patient. Importantly, saliva (expelled in aerosols and droplets) may be a significant factor in person-to-person transmission of SARS-CoV-2, and it has been suggested that NP swab tests remain positive long after patients are infectious (potentially due to detection of inactive virus or remnants of viral RNA in the NP cavity), whereas SARS-CoV-2 viral loads in saliva are highest during the first week of infection, when a person is most infectious. These data suggest that viral loads in saliva may be a good reflection of the transmission potential of patients infected SARS-CoV-2.

Thus, there is a need for a SARS-CoV-2 testing process and workflow that is convenient, simple, rapid, inexpensive, and, as such, can be readily adopted by any testing facility platform that can be scaled to test thousands of individuals per day. The present disclosure satisfies these needs.

SUMMARY OF THE INVENTION

This disclosure provides certain methods for detecting one or more viral polynucleotide sequences—and therefore the presence of the virus—from bodily fluid, and in particular, from a saliva sample, without need for a time consuming and technically difficult RNA extraction process so that the viral polynucleotide may be detected using, for example, PCR, RT-PCR, or RT-qPCR.

Currently, there are no known direct detection of SARS-CoV-2 from saliva that bypasses RNA isolation/purification, and there are several reports of detection from swab/VTM that bypasses RNA isolation/purification (FIG. 1C). With the ultimate goal of providing convenient, scalable, and cost-effective molecular diagnostic testing for >10,000 individuals per day, this disclosure provides a sensitive saliva-based detection method for SARS-CoV-2 that bypasses RNA isolation/purification (FIG. 1D).

In one embodiment, a method of detecting viral polynucleotides (e.g., a corona virus such as SARS-CoV-2 and its variant strains) from a biological sample may comprise, consist essentially of, or consist of the steps of obtaining the biological sample from a subject, heating the biological sample at about 95 degrees Celsius for about 30 minutes, contacting the biological sample with one or more buffering agents and one or more non-ionic detergent to form a test sample, and amplifying target viral polynucleotides in the test sample using polymerase chain reaction (PCR), thereby detecting the viral polynucleotide in the test sample without the need for polynucleotide extraction and purification.

A method of detecting viral polynucleotides (e.g., SARS-CoV-2 or a variant thereof) in a saliva sample comprising, consisting essentially of, or consisting of: combining the saliva sample with TBE at about a 1:1 ratio prior to heating the saliva sample to form a mixture, heating the mixture at about 95 degrees Celsius from about 15 minutes to about 30 minutes, after heating, contacting the heated mixture with one or more non-ionic detergents, wherein the one or more non-ionic detergents are present in a final concentration of about 0.25% to about 1% by weight to provide a test sample, and subjecting the test sample to conditions that amplify target viral polynucleotides in the test sample using RT-qPCR, thereby detecting the viral polynucleotides in the biological sample.

A method of detecting polynucleotides from SARS-CoV-2 in a saliva sample comprising, consisting essentially of, or consisting of: mixing the saliva sample with Tris Borate Ethylenediaminetetraacetic acid (TBE) in a 1:1 ratio prior to heating the saliva sample to form a mixture, heating the mixture at about 95 degrees Celsius for about 15-30 minutes, after heating, contacting the mixture with TWEEN-20, wherein the TWEEN-20 is present in a final concentration of 0.5% or less by weight to provide a test sample; and subjecting the test sample to conditions that amplify target polynucleotides of SARS-CoV-2 in the test sample using RT-qPCR, wherein the target polynucleotides comprise at least a portion of one or more of ORF1ab, N1-gene, N2-gene, and S-gene, thereby detecting the polynucleotides from SARS-CoV-2 in the saliva sample.

In certain embodiments, the biological sample (e.g., saliva sample) may be heated at about 95 degrees Celsius for about 15-30 minutes and then mixed with a buffering agent (e.g., TBE) in a 1:1 ratio to form a mixture. A non-ionic detergent may then be added to the mixture and then amplifying target viral polynucleotides in the sample using appropriate primers and RT-qPCR. Alternatively, the buffing agent may be mixed with the saliva sample at a 1:1 ratio prior to the heating step. Alternatively, both the buffering agent and the non-ionic buffer may be added to the saliva sample prior to heating, with the buffering agent and the saliva sample mixed at a 1:1 ratio.

Also disclosed is a kit for performing any of the methods described herein. For example, certain embodiments of a kit may comprise a collection tube, at least one buffering agent, a non-ionic detergent, a plurality of polynucleotide primers, and one or more polymerase enzymes, and a plurality of oligonucleotides.

The plurality of polynucleotide primers can comprise one or more sets of PCR, RT-PCR, or RT-qPCR primers to amplify at least one sequence of a target polynucleotide from a virus in the sample. Preferably, at least one sequence of a target polynucleotide is from SARS-CoV-2. More preferably, the sequence of target polynucleotide comprises at least a portion of one or more of ORF1a, ORF1b, N-gene, and S-gene.

These and other features and advantages of this invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Definitions

Figure 1:
FIG. 1 illustrates a schematic of SARS-CoV-2 testing. A) The current, widely utilized diagnostic process involves nasopharyngeal (NP) swabs and viral transport media (VTM), followed by RNA extraction and isolation, with RT-qPCR analysis of the samples. NP swabs, VTM, and RNA purification kits have been in short supply at various times. B) In April of 2020, saliva was emergency use authorized (EUA) as a diagnostic sample (Rutgers Clinical Genomics Laboratory TaqPath SARS-CoV-2 Assay; www.fda.gov/media/136875/download), using RNA extraction and isolation, followed by RT-qPCR. C) Other groups have reported direct testing of NP swabs in VTM by RT-qPCR. D) The University of Illinois at Urbana-Champaign (UIUC) protocol involves saliva collection in standard 50 mL conical tubes or 4 ml vials, heating (95° C. for 30 min), followed by addition of buffer and analysis by RT-qPCR.
Figure 1:
Figure 1:
Figure 1:

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five substituents on the ring.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number 1" to "number 2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number 10", it implies a continuous range that includes whole numbers and fractional numbers less than number 10, as discussed above. Similarly, if the variable disclosed is a number greater than "number 10", it implies a continuous range that includes whole numbers and fractional numbers greater than number 10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment). For example, and effective amount of buffering agent may comprise combining a biological sample and the buffering agent in a ratio of about 1:3 w/w to about 3:1 w/w, and an effective amount of non-ionic detergent may comprise a final concentration of about 0.25% to about 1% w/w, or about 0.5% w/w.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. In one embodiment of the methods provided herein, the mammal is a human.

As used herein, the terms "providing", "administering," "introducing," are used interchangeably herein and refer to the placement of a compound of the disclosure into a subject by a method or route that results in at least partial localization of the compound to a desired site. The compound can be administered by any appropriate route that results in delivery to a desired location in the subject.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation, or limitations not specifically disclosed herein.

The terms "polynucleotide" and "nucleic acid" are used interchangeably and mean at least two or more ribo- or deoxy-ribo nucleic acid base pairs (nucleotide) linked which are through a phosphoester bond or equivalent. The nucleic acid includes polynucleotide and polynucleoside. The nucleic acid includes a single molecule, a double molecule, a triple molecule, a circular molecule, or a linear molecule. Examples of the nucleic acid include RNA, DNA, cDNA, a genomic nucleic acid, a naturally existing nucleic acid, and a non-natural nucleic acid such as a synthetic nucleic acid but are not limited. Short nucleic acids and polynucleotides (e.g., 10 to 20, 20 to 30, 30 to 50, 50 to 100 nucleotides) are commonly called "oligonucleotides" or "probes" of single-stranded or double-stranded DNA.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, J M B, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, embodiment of the invention also provides nucleic acid molecules and peptides that are substantially identical to the nucleic acid molecules and peptides presented herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The term "primer" as used herein refers to a short polynucleotide that hybridizes to a target polynucleotide sequence and serves as the starting point for synthesis of new polynucleotides.

Embodiments of the Invention

The disclosure provides a method of detecting target polynucleotides that is non-invasive and, importantly, obviates the need for viral polynucleotide (e.g., RNA) extraction and purification, which often is time consuming only to yield low quality RNA that may be unsuitable for downstream analysis. In various embodiments of the present invention, oligonucleotide primers and probes are used in the methods described herein to amplify and detect target polynucleotide sequences of viral pathogens, and in particular, for detecting polynucleotides from RNA viruses such as a coronavirus (e.g., SARS-CoV-2).

In certain embodiments, a method of detecting polynucleotides in a biological sample may include the steps of obtaining a biological sample from a subject, heating the biological sample at a high temperature for a certain amount of time, contacting the biological sample with one or more buffering agents and/or one or more non-ionic detergents to form a test sample, and amplifying any viral polynucleotides in the test sample using polymerase chain reaction (PCR) to detect the viral polynucleotides without the need for viral polynucleotide extraction and purification.

Preferably, the biological sample may comprise a bodily fluid such as urine, saliva, ascites fluid, blood, serum, plasma, or a combination thereof. In other embodiments, the biological sample is obtained from a mucosal membrane of the subject. In preferred embodiments, the bodily fluid is saliva. Saliva samples can be stored at room temperature for at least 7 days prior to heating and analysis without loss of sensitivity.

The bodily fluid of the biological sample, such as a saliva sample, must be heat treated to inactivate (via lysis) any virus particles in the sample. Preferably, the biological sample is heated at about 25 degrees Celsius, about 35 degrees Celsius, about 45 degrees Celsius, about 55 degrees Celsius, about 65 degrees Celsius, about 75 degrees Celsius, about 85 degrees Celsius, about 90 degrees Celsius, about 95 degrees Celsius, about 100 degrees Celsius, about 105 degrees Celsius, or about 110 degrees Celsius. In other embodiments, the biological sample is heated at about 60 degrees Celsius to about 100 degrees Celsius, or about 65 degrees Celsius to about 95 degrees Celsius, or about 75 degrees Celsius to about 95 degrees Celsius, or about 90 degrees Celsius to about 95 degrees Celsius, or about 95 degrees Celsius. In preferred embodiments, the biological sample is heated at 95 degrees Celsius. In certain preferred embodiments, the biological sample is saliva, and the saliva is heated at about 95 degrees Celsius.

In preferred embodiments, the biological sample is heated for about 1 minute to about 60 minutes, about 1 minute to about 45 minutes, about 1 minute to about 30 minutes, about 5 minutes to about 30 minutes, about 15 minutes to about 30 minutes, or about 30 minutes. In one certain preferred embodiment, the biological sample (with buffering agent, or without buffering agent) is heated at about 95 degrees Celsius for about 25-35 minutes. In another preferred embodiment, the biological sample (with buffering agent, or without buffering agent) is heated at about 95 degrees Celsius for about 15-30 minutes. In still another preferred embodiment, the biological sample (with buffering agent, or without buffering agent) is heated at about 95 degrees Celsius for about 30 minutes. In various embodiments, the heated sample is allowed to cool to room temperature prior to proceeding to any downstream steps. Heating of the saliva sample to about 95 degrees for 15-30 minutes had no effect on the integrity of the polynucleotides in the sample (i.e., no heat degradation of the samples was detected).

The biological sample may be combined with one or more buffering agents prior to amplifying any polynucleotides in the sample. Preferably, the buffering agent is Tris-Borate-EDTA (TBE) (100 mM Tris-HCl pH 8.0, 90 mM boric acid, and 1 mM EDTA) or TE (10 mM Tris-HCl pH 8.0 and 1 mM EDTA), and more preferably, TBE. The buffering agent may be combined with the biological sample (e.g., saliva) prior to the heat inactivation step or after the heat inactivation step. Preferably, the biological sample and the buffering agent are combined in a 1:3 ratio to a 3:1 ratio w/w. More preferably, the biological sample and the buffering agent are combined in 1:1 ratio w/w.

The biological sample also may be combined with a non-ionic detergent prior to amplification of any polynucleotides in the sample, that is, a detergent that includes molecules with head groups that are uncharged. Non-ionic detergents may comprise polyoxyethylene (and related detergents), and glycosidic compounds (e.g., alkyl glycosides). Exemplary alkyl glucosides include octyl β-glucoside, n-dodecyl-β-D-maltoside, beta-decyl-maltoside, and Digitonin. Examples of polyoxyethylene detergents include polysorbates (e.g., polysorbate 20, Polysorbate 40, polysorbate 60, polysorbate 80 (also known as TWEEN-20, TWEEN-40, TWEEN-60, and TWEEN-80, respectively), TRITON-X series (e.g., TRITON X-100), TERGITOL series of detergents (e.g., NP-40), the BRIJ series of detergents (e.g., BRIJ-35, BRIJ-58, BRIJ-L23, BRIJ-L4, BRIJ-010), and PLURONIC F68. Preferably, the non-ionic detergent is a polysorbate, and more preferably, polysorbate 20. Preferably, the non-ionic detergent is present in added to the biological sample to have a final concentration of about 0.25% w/w to about 1% w/w. In certain embodiments, TRITON X-100, polysorbate, or NP-40 are present in a final concentration of about 0.25% w/w to about 1% w/w, or about 0.1% w/w to about 0.5% w/w. In one embodiment, TRITON X-100 is present in a final concentration of about 1% w/w, about 0.5% w/w, or about 0.25% w/w. In another embodiment, a polysorbate is present in a final concentration of about 1% w/w, about 0.5% w/w, about 0.25% w/w, about 0.15% w/w, or about 0.10% w/w. In another embodiment, NP-40 is present in a final concentration of about 1% w/w, about 0.5% w/w, or about 0.25% w/w. In one certain preferred embodiment, TWEEN-20 is present in a final concentration of about 0.25% w/w to about 1% w/w, and more preferably, at about 0.5% w/w.

Contrary to the addition order of the buffering agent, which may be added either before or after the heating step, the non-ionic detergent should be added to the biological sample only after the heating step. Addition of the non-ionic detergent before the heating step results in a reduction or loss of detection of target polynucleotides.

Other embodiments also may include additives to the biological sample (with the buffering agent and non-ionic detergent) such as, but not limited to, RNA stabilizing agents such RNase inhibitor, carrier RNA, glycogen, TCEP, proteinase K, bovine serum albumin (BSA), RNAlater, and PBS-DTT.

After the biological sample is collected and processed according to the methods disclosed herein, the target polynucleotides may be amplified by various methods known to the skilled artisan. Preferably, PCR or a derivative method thereof, is used to amplify nucleic acids of interest (Ghannam, M. G. et al. (2020) "*Biochemistry, Polymerase Chain Reaction (PCR),*" StatPearls Publishing, Treasure Is.; pp 0.1-4; Lorenz, T. C. (2012) "*Polymerase Chain Reaction:*

*Basic Protocol Plus Troubleshooting and Optimization Strategies*," J. Vis. Exp. 2012 May 22; (63):e3998; pp. 1-15).

Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase.

If the target sequence is present in a sample, the primers will bind to the sequence and the polymerase will cause the primers to be extended along the target sequence by adding on nucleotides. By raising and lowering the temperature of the reaction mixture, the extended primers will dissociate from the target nucleic acid to form reaction products, excess primers will bind to the target nucleic acid and to the reaction products and the process is repeated, thereby generating amplification products. Cycling parameters can be varied, depending on the length of the amplification products to be extended. An internal positive amplification control (IAC) can be included in the sample, utilizing oligonucleotide primers and/or probes. The IAC can be used to monitor both the conversion process and any subsequent amplification.

An artisan of ordinary skill in the art may design and prepare primers that are appropriate for amplifying a target sequence in view of the information disclosed herein. The length of the amplification primers for use in the dis closed methods is dependent upon on several factors. These include the nucleotide sequence identity and the temperature at which these nucleic acids are hybridized or used during nucleic acid amplification. The considerations necessary to determine a preferred length for an amplification primer of a sequence identity are well known to the person of ordinary skill in the art.

For example, primers that amplify a nucleic acid molecule can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis or real-time PCR), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 40 nucleotides in length.

In preferred embodiments, the PCR technique used to amplify a target polynucleotide is real-time quantitative PCR (RT-qPCR) or quantitative PCR (qPCR). Quantitative PCR is characterized in that a PCR product is marked and tracked through a fluorescent dye or a specific probe marked by fluorescence to carry out a real-time monitoring reaction, and the product is analyzed using software adapted to monitor the reaction, such that the initial concentration of a target polynucleotide in a sample may be calculated. A reverse transcription reaction is involved in the PCR reaction process when the target polynucleotide is an RNA nucleic acid and the resultant amplified product may be analyzed using CT-values (see, for example, Chan et al., *Improved Molecular Diagnosis of COVID-19 by the Novel, Highly Sensitive and Specific COVID-19-RdRp/Hel Real-Time Reverse Transcription-PCR Assay Validated In Vitro and with Clinical Specimens*. J Clin Microbiol. 2020 May; 58(5): e00310-20).

In some embodiments, the total reaction volume of a PCR reaction is 10 µl or less. Preferably, the reaction volume comprises a 1:1 ratio of heat-treated saliva sample mixed with PCR reaction components (e.g., buffers, polymerases, nucleotides, etc.).

In some embodiments, the target viral polynucleotide may include a polynucleotide from a corona virus such as, but not limited to, SARS-CoV-2, CoV-229E, CoV-NL63, CoV-HKU1, CoV-OC43, MERS or SARS. Preferably, the one or more target genes are from SARS-CoV-2 and/or its variants (e.g., B.1.1.7, B.1.351, B.1.525, B.1.617, B.1.429, B.1.427, B.1.1.207, and P.1). In certain preferred embodiments, target polynucleotides include one or more of ORF1a, ORF1b, N1-gene, N2-gene, S-gene, or portions thereof.

Amplification of nucleic acids can be detected by a number of methods well-known in the art such as gel electrophoresis, column chromatography, hybridization with a probe, sequencing, melting curve analysis, or "real-time" detection.

In one approach, sequences from two or more fragments of interest are amplified in the same reaction vessel (i.e., "multiplex PCR"). Detection can take place by measuring the endpoint of the reaction or in "real time." For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the TaqMan® system and the use of intercalating dyes for double stranded nucleic acid.

In some embodiments, amplified nucleic acids are detected by hybridization with a specific probe. Probe oligonucleotides, complementary to a portion of the amplified target sequence may be used to detect amplified fragments. Hybridization may be detected in real time or in non-real time. Designing oligonucleotides to be used as hybridization probes can be performed in a manner similar to the design of primers. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 60 nucleotides in length. In some embodiments, hybridization probes may be used to identify a target polynucleotide.

Exemplary probes that may be detectably labeled by methods known in the art include, e.g., fluorescent dyes (e.g., Cy5®, Cy3®, FITC, rhodamine, lanthamide phosphors, Texas red, FAM, JOE, Cal Fluor Red 610®, Quasar 670°), $^{32}P$, $^{35}S$, $^{3}H$, $^{14}C$, $^{125}I$, $^{131}I$, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., DYNABEADS), biotin, dioxigenin, or haptens and proteins for which antisera or monoclonal antibodies are available.

In certain embodiments, the lower limit of detection about 5000 viral copies/mL, about 4500 viral copies/mL, about 4000 viral copies/mL, about 3500 viral copies/mL, about 3000 viral copies/mL, about 2500 viral copies/mL, about 2000 viral copies/mL, about 1500 viral copies/mL, about 1000 viral copies/mL, about 900 viral copies/mL, about 800 viral copies/mL, about 700 viral copies/mL, about 600 viral copies/mL, about 500 viral copies/mL, about 400 viral copies/mL, about 300 viral copies/mL, about 200 viral copies/mL, or about 100 viral copies/mL. In other embodiments, the lower limit of detection is about 100-5000 viral copies/mL. In still other embodiments, the lower limit of detection is about 100-500 viral copies/mL.

Some embodiments include the use of a multiplex RT-qPCR assay. For example, certain embodiments of a method of the disclosure may comprise incubating saliva samples at 95° C. for 30 min, cooling the sample to room temperature, mixing the heat-treated saliva sample with 2×TBE+1% Tween-20 buffer at 1:1 dilution ratio to form a test sample, subjecting the test sample to conditions that amplify viral polynucleotides in the test sample using RT-qPCR. The method further may comprise analyzing the test sample for the presence of amplified viral polynucleotides in the test sample.

In some embodiments, the multiplex RT-qPCR assay may use the TaqPath RT-PCR COVID-19 kit (Thermo Fisher CN A47814) together with the TaqPath 1-step master mix—No ROX (Thermo Fisher CN A28523). For example, RT-qPCR reactions may comprise 5 uL template+5 uL of reaction mix (2.5 uL TaqPath 1-step master mix, 0.5 uL TaqPath primer/probe mix, 1.0 uL MS2, and 1.0 RNase-free water). The assay may be performed in 384-well reaction plates in a QuantStudio 7 system (Applied Biosciences). The RT-qPCR may be conducted using the standard mode, consisting of, for example, a hold stage at 25° C. for 2 min, 53° C. for 10 min, and 95° C. for 2 min, followed by 40 cycles of a PCR stage at 95° C. for 3 sec then 60° C. for 30 sec; with a 1.6° C./sec ramp up and ramp down rate.

One of ordinary skill in the art will recognize the temperatures, the length of time at such temperatures, and the number of cycles to which a polynucleotide sample (e.g., DNA, RNA) must be subject to effectuate amplification of polynucleotide for the different methods of using an apparatus of the invention, e.g., screening, identification, quantification, etc. For example, in a preferred embodiment, denaturing temperatures are between 90° C. and 95° C., annealing temperatures are between 55° C. and 65° C., and elongation temperatures are dependent on the polymerase chosen (e.g., the optimal elongation temperature is about 72° C. for Taq polymerase). Also, the artisan or ordinary skill will recognize that that "hot starts" often begin PCR amplification methods, and that a final incubation of a polynucleotide sample at 75° C. may optionally be added to the end of any amplification method. For example, although a typical cycling profile is ~94° C. for 1 min., 60° for 1 min., 72° for 1 min. (a typical rule for a 72° C. elongation is 1 minute for each 1000 base pairs being amplified), etc., an artisan or ordinary skill will recognize that the duration of time a sample remains at a certain temperature is dependent on the volume of the reaction, the concentration of the polynucleotide, etc. An artisan or ordinary skill will recognize that shorter durations at each temperature may be sufficient. (See, for example, U.S. Pat. Pub. No. 2011/0189736).

In one certain embodiment, a method of detecting viral polynucleotides from a biological sample may comprise, consist essentially of, or consist of the steps of obtaining the biological sample from a subject, heating the biological sample at about 95 degrees Celsius for about 15-30 minutes, contacting the biological sample with one or more buffering agents to form a test sample, and subjecting the test sample to conditions that amplify target viral polynucleotides in the test sample using polymerase chain reaction (PCR), thereby detecting the viral polynucleotides in the biological sample.

In one certain embodiment, a method of detecting viral polynucleotides from a biological sample may comprise, consist essentially of, or consist of the steps of obtaining the biological sample from a subject, heating the biological sample at about 95 degrees Celsius for about 15-30 minutes, contacting the biological sample with one or more buffering agents and one or more non-ionic detergents to form a test sample, and subjecting the test sample to conditions that amplify target viral polynucleotides in the test sample using polymerase chain reaction (PCR), thereby detecting the viral polynucleotides in the biological sample.

In another embodiment, a method of detecting viral polynucleotides in a biological sample may comprise, consist essentially of, or consist of the steps of heating a biological sample from a subject at about 95 degrees Celsius for about 25-35 minutes, contacting the biological sample with one or more buffering agents and one or more non-ionic detergents to provide a test sample; subjecting the test sample to conditions that amplify viral polynucleotides in the heated biological test sample, if present, using a polymerase chain reaction (PCR), and analyzing the test sample for the presence of amplified viral polynucleotides in the biological sample.

In another embodiment, a method of detecting viral polynucleotides in a saliva sample may comprise, consist essentially of, or consist of the steps of combining a saliva sample, taken from a subject, with TBE at about a 1:1 ratio prior to heating the saliva sample to form a mixture, heating the mixture at about 95 degrees Celsius for about 15-30 minutes, after heating, contacting the heated mixture with one or more non-ionic detergents, wherein the one or more non-ionic detergents are present in a final concentration of about 0.25% to about 1% by weight to provide a test sample, and subjecting the test sample to conditions that amplify target viral polynucleotides, if present, in the test sample using RT-qPCR, thereby detecting the viral polynucleotides in the biological sample.

In another embodiment, a method of detecting viral nucleic acid in a saliva sample may comprise, consist essentially of, or consist of the steps of mixing a saliva sample with TBE in a 1:1 ratio prior to heating the saliva sample to form a mixture, heating the mixture at about 95 degrees Celsius for about 15-30 minutes, contacting the heated mixture with TWEEN-20, wherein the TWEEN-20 is present in a final concentration of 0.5% or less by weight to provide a test sample, and subjecting the test sample to conditions that amplify target polynucleotides of SARS-CoV-2, if present, in the test sample using RT-qPCR, wherein the amplified polynucleotides comprise one or more of ORF1ab, N1-gene, N2-gene, S-gene, and portions thereof.

Some embodiments comprise, consist essentially of, or consist of a method of detecting polynucleotides from SARS-CoV-2 in a saliva sample comprising heating the saliva samples at about 95 degrees Celsius for about 15-30 minutes, mixing the saliva sample, after the heating step, with 2×TBE and 1% TWEEN-20 in a 1:1 ratio to form a mixture, wherein the 2×TBE and the 1% TWEEN-20 are present in the mixture at a final concentration of 1× and 0.5% or less by weight, respectively, subjecting the mixture to conditions that amplify target polynucleotides of SARS-CoV-2 in the mixture using RT-qPCR, wherein the target polynucleotides comprise at least a portion of one or more of ORF1ab, N1-gene, N2-gene, and S-gene, thereby detecting the polynucleotides from SARS-CoV-2 in the saliva sample.

In some embodiments, certain steps of the method, such as the mixing, contacting, and subjecting/amplification steps may be partially or fully automated. In some embodiments, all the steps of the methods described herein may be partially or fully automated.

This disclosure also provides a kit for the detection of one or more viral polynucleotides present in a biological sample using polymerase chain reaction assay. An exemplary kit may include one or more primer pairs such that the primer pair can detect and/or amplify target viral polynucleotides, if present, in the sample. In some embodiments, the target viral polynucleotide may include a polynucleotide from a corona virus such as, but not limited to, SARS-CoV-2, CoV-229E, CoV-NL63, CoV-HKU1, CoV-OC43, MERS or SARS. Preferably, the primer pairs can detect one or more target genes of SARS-CoV-2 and its variants (e.g., B.1.1.7, B.1.351, B.1.525, B.1.617, B.1.429, B.1.427, B.1.1.207, and P.1). In certain embodiments, the target genes detected from SARS-CoV-2 include at least one or more of ORF1a, ORF1b, N-gene (N1-gene, N2-gene), E-gene, M-gene, and S-gene. Preferably, the PCR assay is RT-qPCR. Amplification products may be detected using methods that are well known to a person of ordinary skill in the art.

An exemplary kit also may include a buffering agent such as TE or TBE, one or more non-ionic detergents such as a polysorbate (e.g., TWEEN-20, TWEEN-80), optionally one or more sample additives, one or more polymerase (e.g., DNA polymerase, reverse transcriptase), any reagents for performing PCR or RT-PCR, and one or more vial/containers to hold each component as well as to collect and process the saliva sample.

Another embodiment of a kit of the disclosure may comprise one or more collection tubes, at least one buffering agent, at least one non-ionic detergent, a plurality of RT-qPCR primers, one or more RT-qPCR reagents, and one or more polymerases.

In another embodiment, the primers of the kit are configured to amplify and/or detect target polynucleotides from SARS-CoV-2. In particular, at least one sequence of the target polynucleotides comprises one or more of ORF1ab, N1-gene, N2-gene, and S-gene.

One embodiment of a kit of the disclosure, comprises a commercially available polynucleotide amplification and/or detection kit such as, for example, TaqPath™ COVID-19 Combo Kit (ThermoFisher).

Other commercially available primers and probes useful in targeting the N1, N2, and RP genes may be purchased, for example, purchased from Integrated DNA Technologies: nCOV_N1 Forward Primer Aliquot (CN 10006830), nCOV_N1 Reverse Primer Aliquot (CN 10006831), nCOV_N1 Probe Aliquot (CN 10006832), nCOV_N2 Forward Primer Aliquot (CN 10006833), nCOV_N2 Reverse Primer Aliquot (CN 10006834), nCOV_N2 Probe Aliquot (CN 10006835), RNase P Forward Primer Aliquot (CN 10006836), RNase P Reverse Primer Aliquot (CN 10006837), RNase P Probe Aliquot (CN 10006838).

Development of a Direct Saliva-to-RT-qPCR Process for Detection of SARS-CoV-2.

While SARS-CoV-2 has been identified in the nasopharynx, collecting NP samples is neither trivial nor innocuous, and for repeat testing to track disease progression within a given patient this method may prove unreliable, due to inconsistencies in repeated sampling and potential formation of scar tissue, altogether resulting in possible false-negatives. Compounding these anatomic limitations, the procedure for NP sample collection is invasive, further reducing patient compliance for repeated and serial sampling.

Saliva may serve as an important mediator in transmitting SARS-CoV-2 between individuals via droplets and aerosols, and thus viral loads in saliva may serve as a highly relevant correlate of transmission potential. However, saliva is comprised of constituents that may hinder virus detection by RT-qPCR, such as degradative enzymes. As such, we sought to identify conditions that could take advantage of the many positives of saliva while overcoming potential limit of detection challenges with this collection medium.

For the optimization phase of this work we utilized two versions of inactivated SARS-CoV-2, one inactivated through gamma($\gamma$)-irradiation ($5 \times 10^6$ RADs) and one inactivated through heat (65° C., 30 min). For the detection of SARS-CoV-2, we utilized the commercially available TaqPath RT-PCR COVID-19 kit, developed and marketed by Thermo Fisher Scientific. This multiplex RT-qPCR kit targets the ORF1ab (replication), N-gene (nucleocapsid), and S-gene (spike) of SARS-CoV-2. To reduce cost and extend reagent usage, we performed RT-qPCR reactions at half the suggested reaction mix volume.

Heat Treatment.

Figure 2:
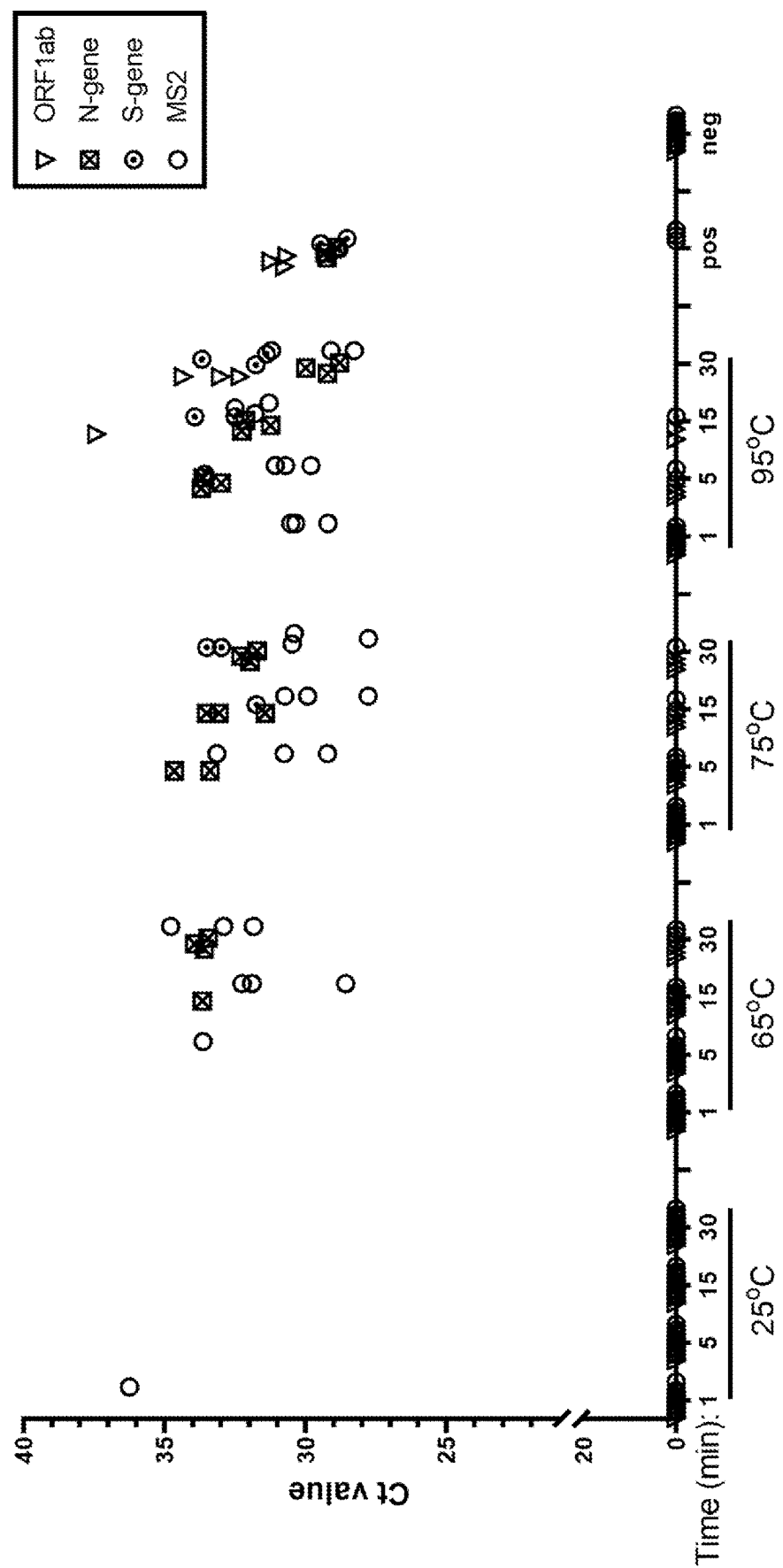
FIG. 2 illustrates the effect of heat on SARS-CoV-2 detection. γ-irradiated SARS-CoV-2 (from BEI, used at $1.0 \times 10^4$ viral copies/mL) was spiked into fresh human saliva (SARS-CoV-2 negative). Samples diluted 1:1 with 2× Tris-borate-EDTA (TBE) buffer (0.5 mL in 50 mL conical tubes) were incubated at 25° C. (ambient temperature), or in a hot water bath at 65° C., 75° C., or 95° C., for 1, 5, 15, or 30 min. All saliva samples were spiked with purified MS2 bacteriophage (1:40 MS2:sample) as an internal control. Virus-spiked saliva samples, a positive control (pos; SARS-CoV-2 positive control, $5.0 \times 10^3$ copies/mL, no MS2) and a negative control (neg; water, no MS2) were directly analyzed by RT-qPCR, in triplicate, for SARS-CoV-2 ORF1ab (open triangle), N-gene (open square), and S-gene (circle with inner dot), and MS2 (open circle). Undetermined Ct values are plotted at 0.

Up-front heating of freshly collected saliva samples is attractive as a simple method to inactivate the virus without having to open the collection vessel. Indeed, heat treatment is often used to inactivate saliva patient samples, thus conferring added biosafety by decreasing the likelihood of viral transmission via sample handling by personnel. Common conditions for SARS-CoV-2 inactivation are heating at 56-60° C. for 30-60 min, although other temperature and times have been examined. Using intact, $\gamma$-irradiated SARS-CoV-2 spiked into fresh human saliva (that was confirmed to be SARS-CoV-2 negative), we observed dramatic time- and temperature-dependent improvement in SARS-CoV-2 detection by direct RT-qPCR, without the use of RNA extraction. When incubated at ambient temperature (no heat treatment), no SARS-CoV-2 genes were detectable (FIG. 2).

As temperature and incubation time were increased, substantial improvement in virus detection was observed, with 100% identification of all SARS-CoV-2 genes, in all replicate samples, being detected following a 30 min incubation at 95° C. Importantly, a short heating time (5 minutes) at 95° C. (as has been examined by others) does not allow for sensitive detection; the 30 minute duration is essential, as it is likely that this extended heating inactivates components of saliva that inhibit RT-qPCR. Thus, proper heating of patient samples allows for virus detection without the need for RNA extraction, with the added benefit of inactivating the samples, thus substantially reducing biohazard risks. Heat inactivation had no effect on sample integrity.

Saliva Collection Buffer.

Figure 3:
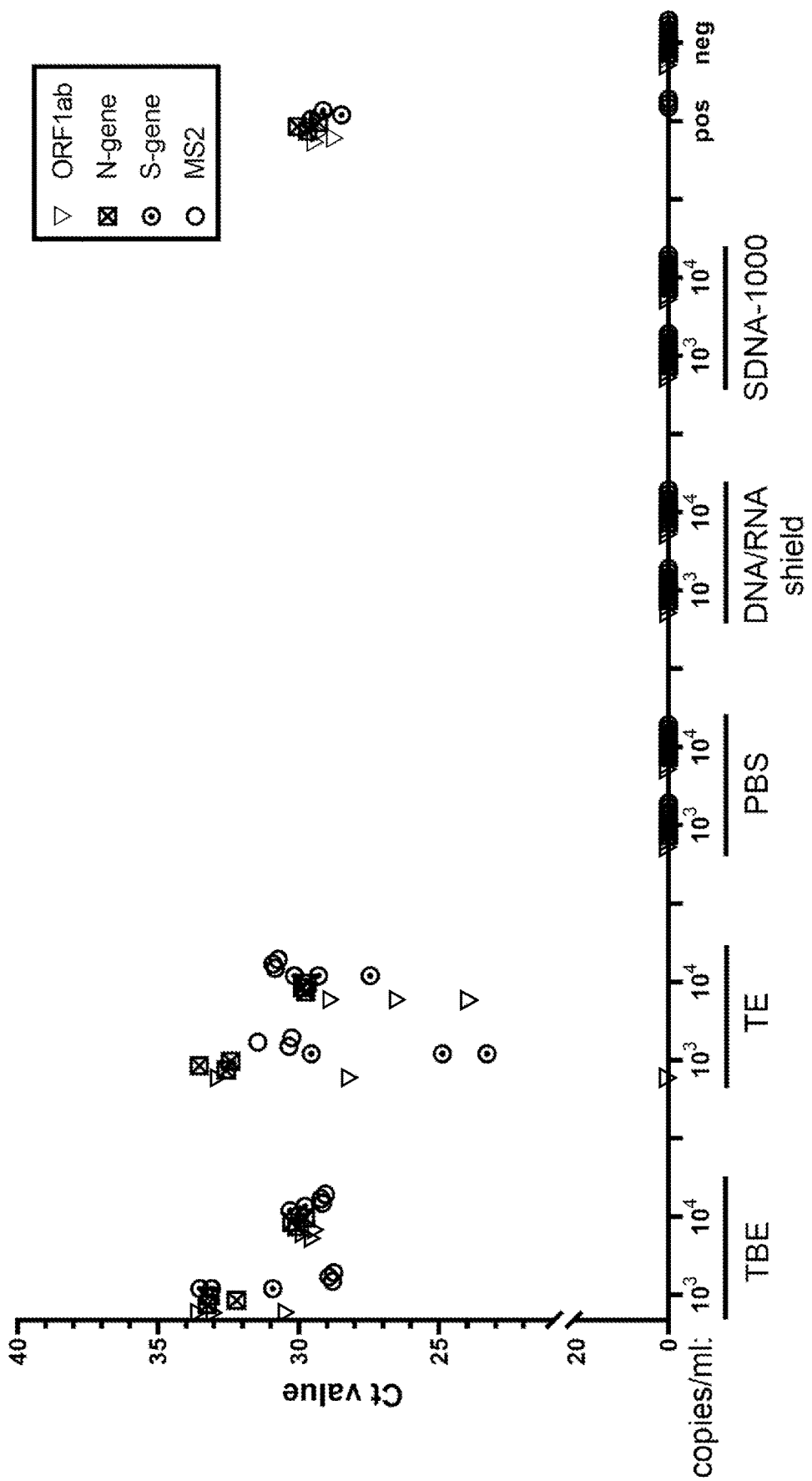
FIG. 3 illustrates (A) the effect of collection buffer on SARS-CoV-2 detection. γ-irradiated SARS-CoV-2 (from BEI, at $1.0 \times 10^3$ or $1.0 \times 10^4$ viral copies/mL) was spiked into fresh human saliva (SARS-CoV-2 negative) and combined at a 1:1 ratio with Tris-Borate-EDTA (TBE), Tris-EDTA (TE), Phosphate Buffered Saline (PBS), DNA/RNA shield (Zymo Research), or SDNA-1000 (Spectrum Solutions) such that the final concentration of each buffer was 1×. Samples (0.5 mL in 50 mL conical tubes) were incubated in a hot water bath at 95° C. for 30 min. (B) Detergent optimization. γ-irradiated SARS-CoV-2 ($1.0 \times 10^4$ viral copies/mL) was spiked into fresh human saliva (SARS-CoV-2 negative) and combined 1:1 with TBE buffer at a final working concentration of 1×. Samples were treated with detergents (Triton X-100, 1%, 0.5%, 0.25%; Tween 20, 1%, 0.5%, 0.25%; NP-40, 2%, 1%, 0.5%) after heating at 95° C. for 30 min. All saliva samples were spiked with purified MS2 bacteriophage (1:40 MS2:sample) as an internal control. Virus-spiked saliva samples, a positive control (pos; SARS-CoV-2 positive control, $5.0 \times 10^3$ copies/mL, no MS2) and a negative control (neg; water, no MS2) were directly analyzed by RT-qPCR, in triplicate, for SARS-CoV-2 ORF1ab (open triangle), N-gene (open square), and S-gene (circle with inner dot), and MS2 (open circle). Undetermined Ct values are plotted at 0.
Figure 3:
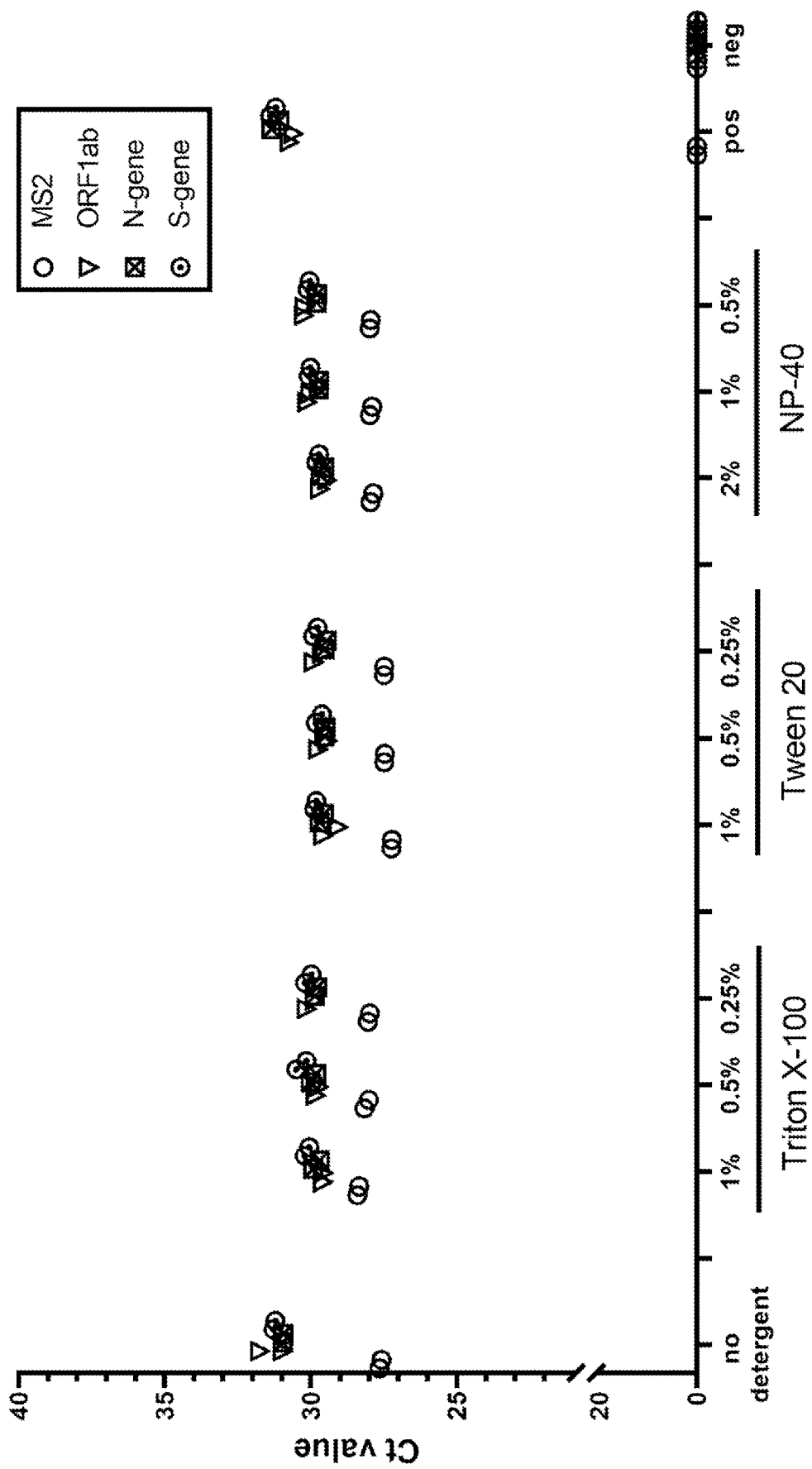

We next sought to evaluate saliva collection buffers as a means to enhance viral RNA stability, but also to increase uniformity between saliva samples and to decrease sample viscosity. In conjunction with RNA isolation/purification, other groups have utilized protocols whereby saliva was provided by a patient and soon thereafter combined with the collection buffer; reported collection buffers include Phosphate Buffered Saline (PBS), DNA/RNA Shield, and Tris-EDTA (TE). Using intact, $\gamma$-irradiated SARS-CoV-2 spiked into fresh human saliva, which was then heat treated at 95° C. for 30 min, we observed outstanding virus detection when saliva samples were combined with either Tris-Borate-EDTA (TBE) or TE buffer (FIG. 3A).

Figure 7:
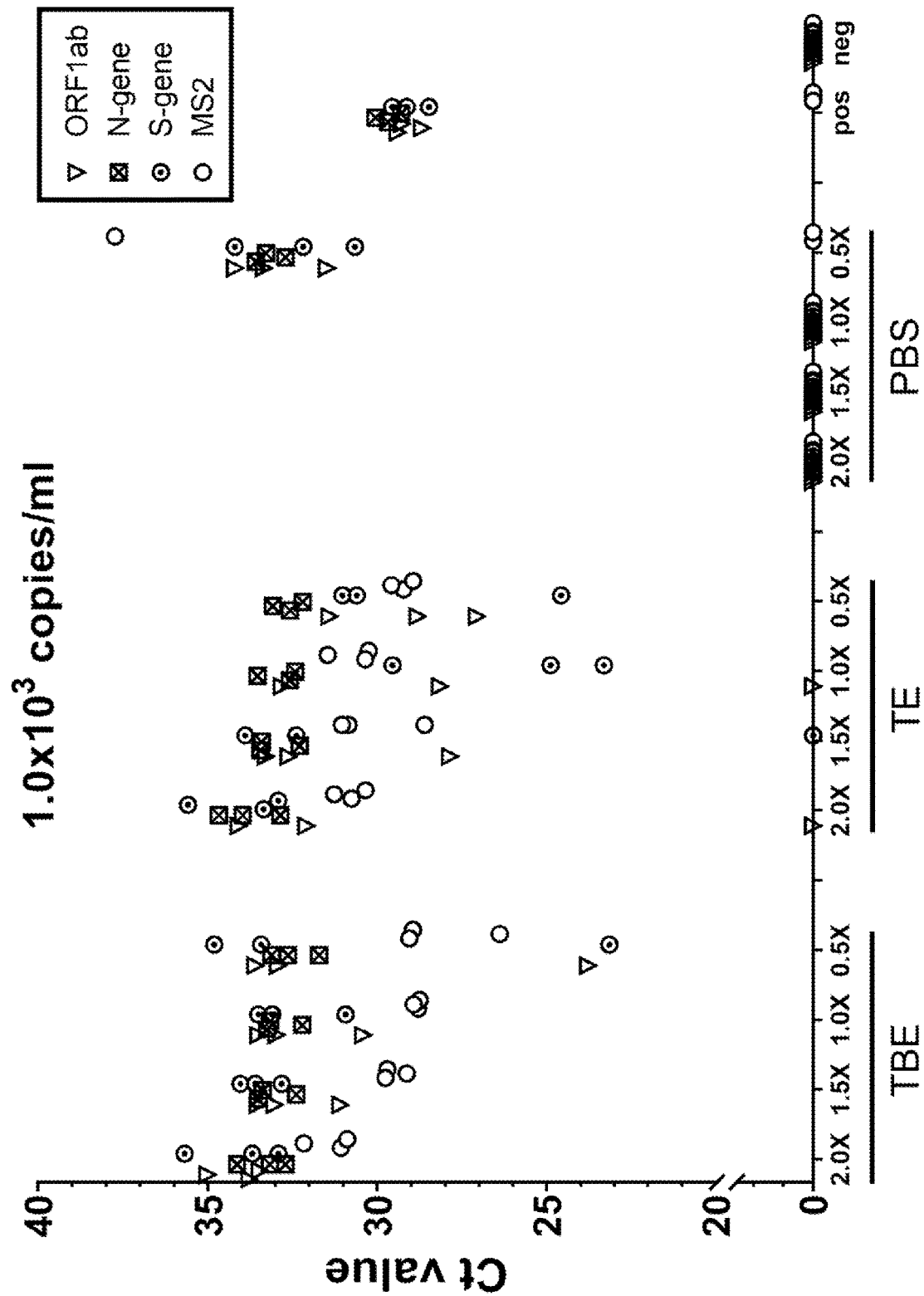
FIG. 7 illustrates the saliva collection buffer titration. γ-irradiated SARS-CoV-2 ($1.0 \times 10^3$ (a) or $1.0 \times 10^4$ (b) viral copies/mL) was spiked into fresh human saliva (SARS-CoV-2 negative) and combined with Tris-Borate-EDTA buffer (TBE), Tris-EDTA buffer (TE), or Phosphate Buffered Saline (PBS), at a final working concentration of 2×, 1.5×, 1×, or 0.5×. Samples (0.5 mL in 50 mL conical tubes) were incubated in a hot water bath at 95° C. for 30 min. All saliva samples were spiked with purified MS2 bacteriophage (1:40 MS2:sample) as an internal control. Virus-spiked saliva samples, a positive control (pos; SARS-CoV-2 positive control, $5.0 \times 10^3$ copies/mL, no MS2) and a negative control (neg; water, no MS2) were directly analyzed by RT-qPCR, in triplicate, for SARS-CoV-2 ORF1ab (open triangle), N-gene (open square), and S-gene (circle with inner dot), and MS2 (open circle). Undetermined Ct values are plotted at 0.
Figure 7:
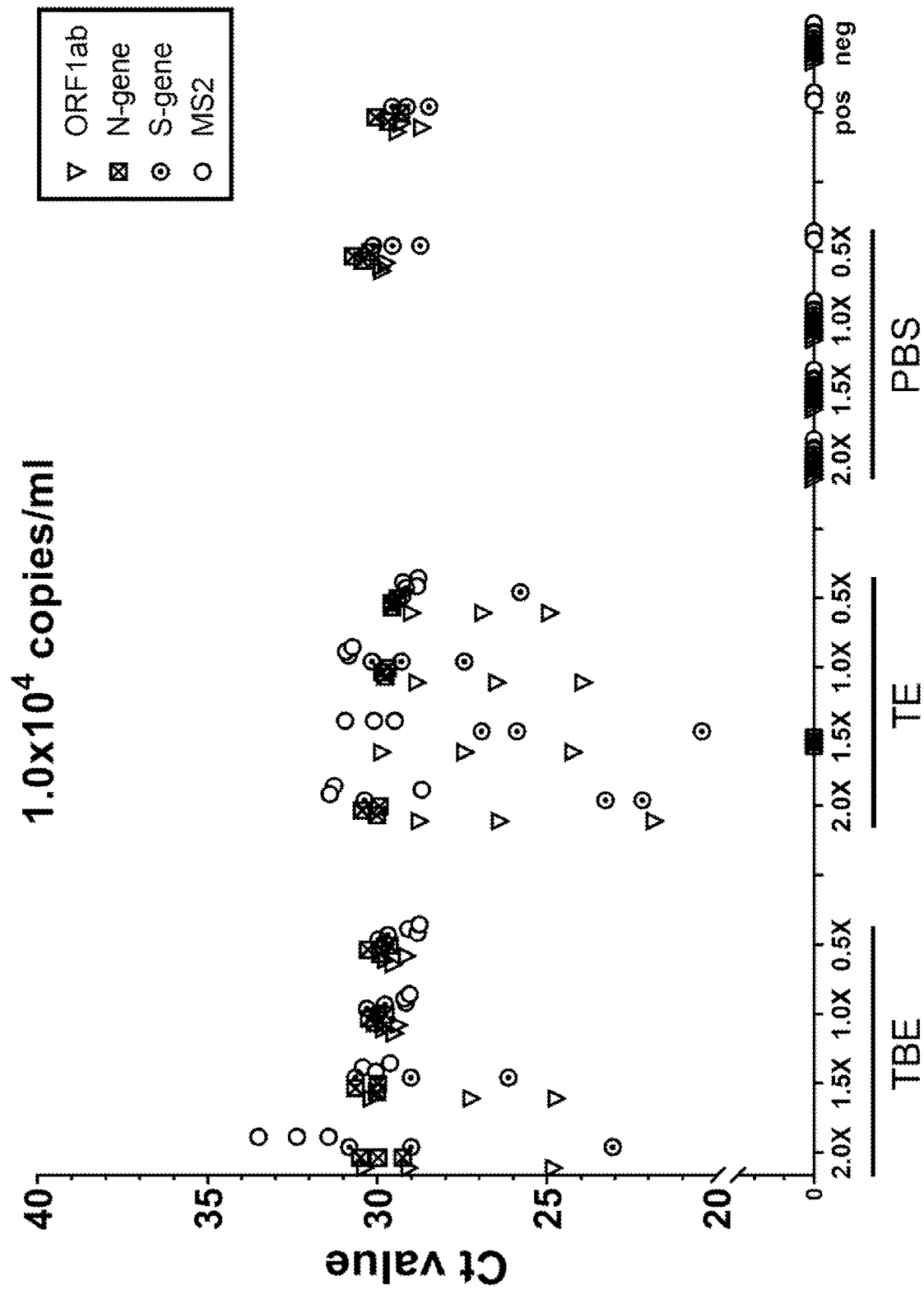

Comparable Ct values were observed between TBE and TE buffer, but TE yielded greater variability between individual gene replicates, whereas TBE buffer yielded highly clustered data. In stark contrast, combining saliva with PBS or two commercially available buffers (DNA/RNA Shield, SDNA-1000), completely abrogated viral detection, including the MS2 bacteriophage internal control, indicating that these buffers directly interfere with the RT-qPCR reaction itself. TBE, TE, and PBS were further titrated with different concentrations of SARS-CoV-2, where similar trends were observed, namely, greater replicate variability with TE buffer, and no virus detection with PBS (FIG. 7). Thus, when saliva samples are combined with TBE buffer to a final working concentration of 1×, SARS-CoV-2 is detectable in saliva without RNA extraction; TE buffer is also suitable but more variability is observed. These findings further suggest that while PBS and commercially available buffers may be appropriate for samples that are processed via RNA extraction, these agents are incompatible with direct saliva-to-RT-qPCR.

Sample Additives.

Figure 8:
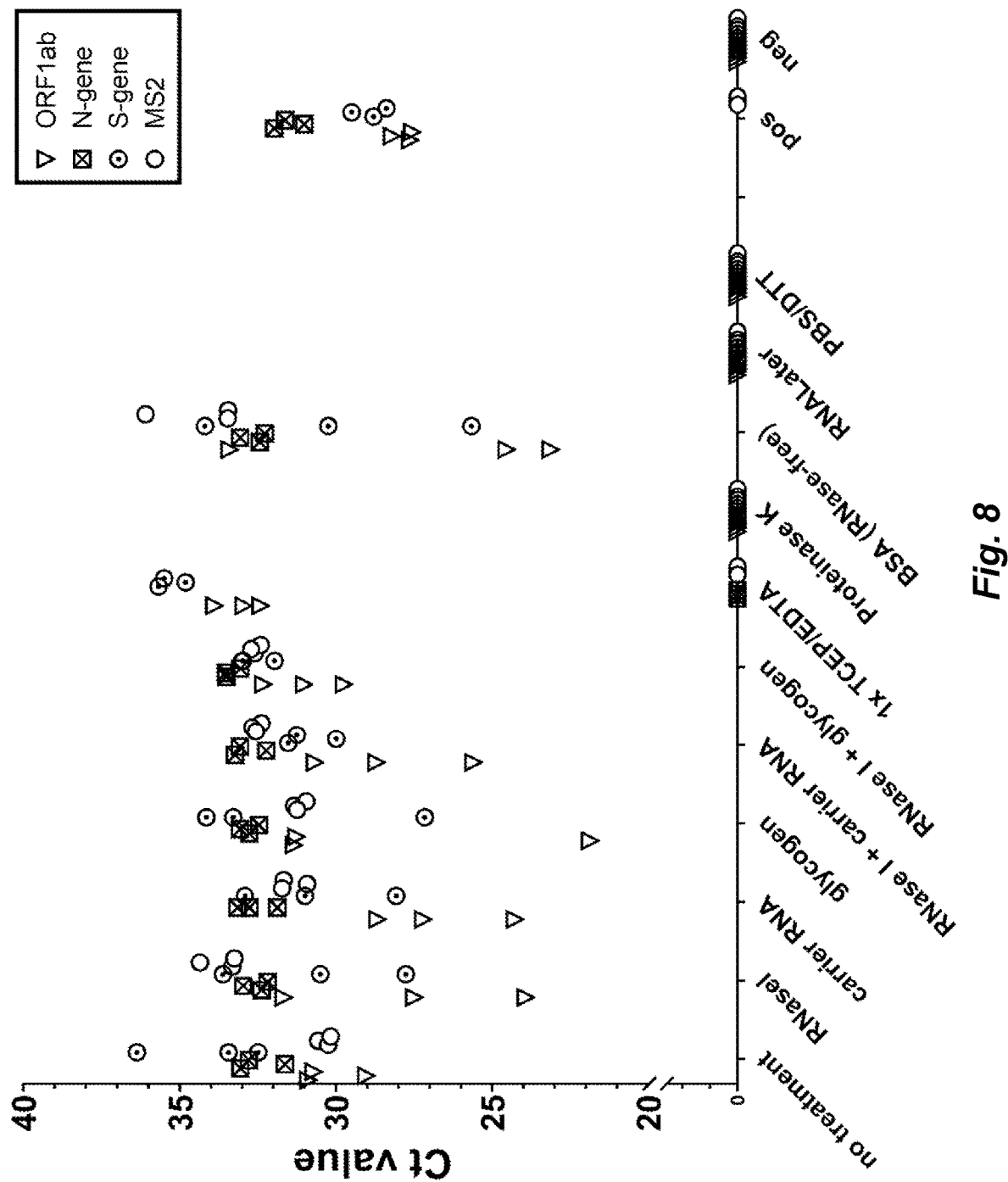
FIG. 8 illustrates the RNA stabilizing additive optimization. γ-irradiated SARS-CoV-2 ($1.0 \times 10^4$ viral copies/mL) was spiked into fresh human saliva (SARS-CoV-2 negative) and combined with TBE buffer, at a final working concentration of 1×. Samples (0.5 mL in 50 mL conical tubes) were incubated in a hot water bath at 95° C. for 30 min. Following heat treatment, virus-spiked saliva was combined with various RNA stabilizing agents, including RNaseI (1 U/μL), carrier RNA (0.05 μg/mL), glycogen (1 μg/μL), TCEP/EDTA (1×), Proteinase K (5 μg/μL), RNase-free BSA (1.25 mg/mL), RNAlater (1:1 ratio in place of TBE), or PBS/DTT (6.5 mM DTT in PBS, diluted 1:1 in place of TBE). All saliva samples were spiked with purified MS2 bacteriophage (1:40 MS2:sample) as an internal control. Virus-spiked saliva samples with or without additives, a positive control (pos; SARS-CoV-2 positive control, $5.0 \times 10^3$ copies/mL, no MS2) and a negative control (neg; water, no MS2) were directly analyzed by RT-qPCR, in triplicate, for SARS-CoV-2 ORF1ab (open triangle), N-gene (open square), and S-gene (circle with inner dot), and MS2 (open circle). Undetermined Ct values are plotted at 0.
Figure 9:
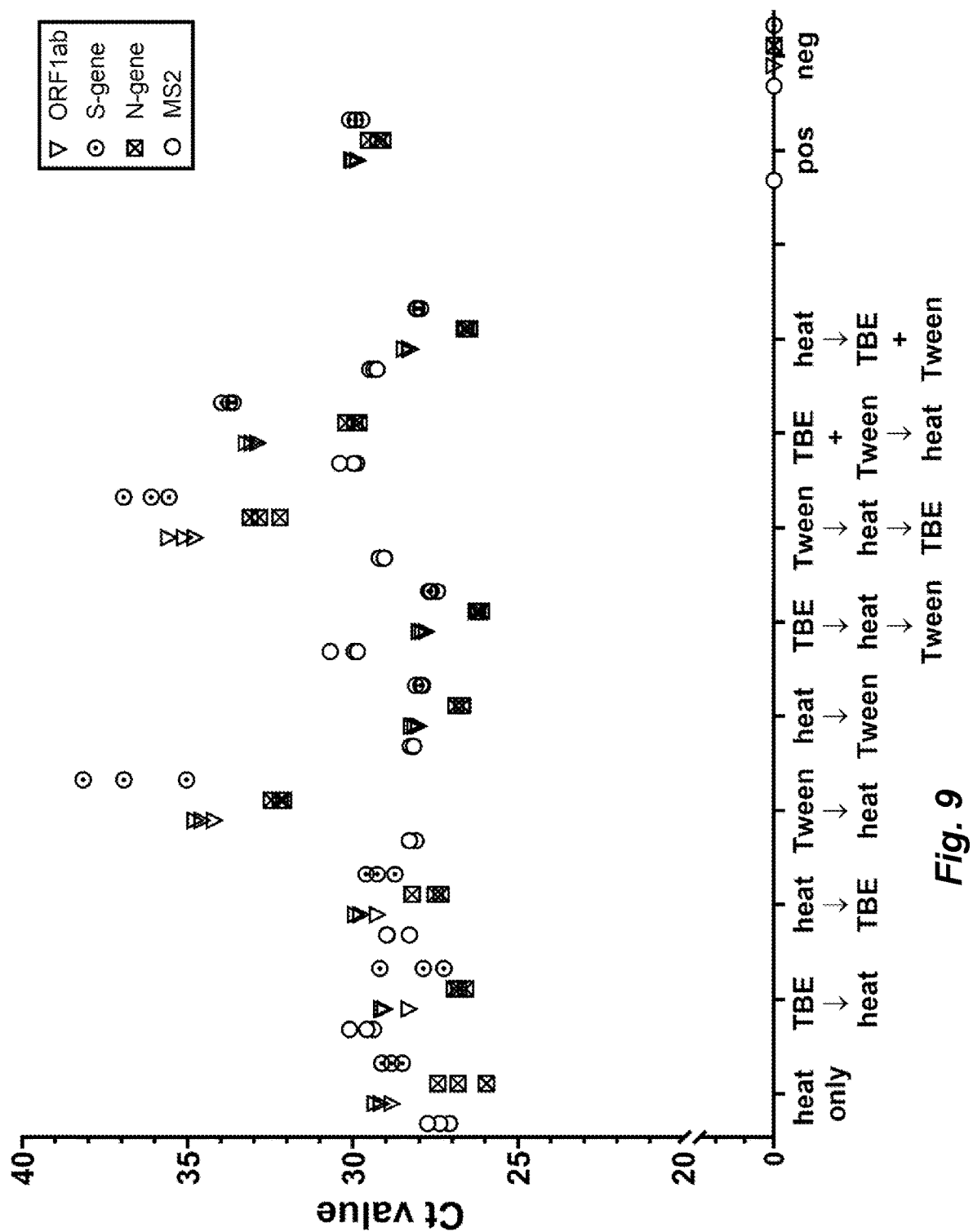
FIG. 9 illustrates the workflow of TBE and Tween-20 addition in relation to heat. γ-irradiated SARS-CoV-2 ($1.0 \times 10^5$ viral copies/mL) was spiked into fresh human saliva (SARS-CoV-2 negative) and combined with TBE buffer (1:10, final concentration 1×) and Tween 20 (1:20, final concentration 0.5%) alone or in combination, before or after heat treatment at 95° C. for 30 min. All saliva samples were spiked with purified MS2 bacteriophage (1:40 MS2:sample) as an internal control. Virus-spiked saliva samples, a positive control (pos; SARS-CoV-2 positive control, $5.0 \times 10^3$ copies/mL, no MS2) and a negative control (neg; water, no MS2) were directly analyzed by RT-qPCR, in triplicate, for SARS-CoV-2 ORF1ab (open triangle), N-gene (open square), and S-gene (circle with inner dot), and MS2 (open circle). Undetermined Ct values are plotted at 0.

In addition to saliva collection buffers, various additives have been explored for their ability to enhance SARS-CoV-2 detection. Therefore, detergents, including Triton X-100, Tween 20, and NP-40 (FIG. 3B), as well as various RNA stabilizing agents, including RNase inhibitor, carrier RNA, glycogen, TCEP, proteinase K, bovine serum albumin (BSA), RNAlater, and PBS-DTT (FIG. 8) were examined. Notably, modest improvements in viral detection were observed with all detergents tested (~2 Ct, FIG. 3B) and with addition of carrier RNA, RNase inhibitor, and BSA (FIG. 8), These additives slightly improve virus detection, without interfering with RT-qPCR; in addition, if clinical saliva specimens are especially viscous, addition of detergent may improve ease of sample handling. However, inclusion of detergents prior to heat treatment completely inhibited viral detection, emphasizing the importance of adding detergents after heat treatment, if they are to be included (FIG. 9).

Of the detergents tested, Tween 20 was chosen for incorporation into the standard sample processing protocol, given its ease of handling and cost. When samples were treated with Tween 20 and TBE (alone or in combination, either before or after heating) the ideal workflow for virus detection, as defined by the lowest Ct values with the greatest clustering of individual replicates, was TBE buffer before heating, and Tween 20 after heating (FIG. 9). However, it is important to note that comparable results were obtained when TBE was added after heating (FIG. 9), suggesting flexibility in when TBE buffer can be included during sample processing. Altogether, the safest and most streamlined protocol would be the following: collection of saliva samples, heat at 95° C. for 30 min, add TBE buffer and Tween 20, followed by RT-qPCR.

Limit of Detection.

Using the optimized protocol of addition of TBE (or TE) buffer at a 1:1 ratio with saliva, followed by heat treatment at 95° C. for 30 min and addition of Tween 20 to a final concentration of 0.5%, the limit of detection (LOD) was determined. Other reports have suggested that SARS-CoV-2 is shed into saliva at a remarkably wide range from 10,000-10,000,000,000 copies/mL. While the LOD of SARS-CoV-2 approved diagnostic methods can vary considerably (500-80,000 viral copies/mL) and are not always reported, the best LOD values for SARS-CoV-2 using RNA extraction protocols appear to be approximately 1000 copies/mL. Similarly, a LOD of 5610 copies/mL was found for SARS-CoV-2 detection in saliva using RNA purification.

Figure 4:
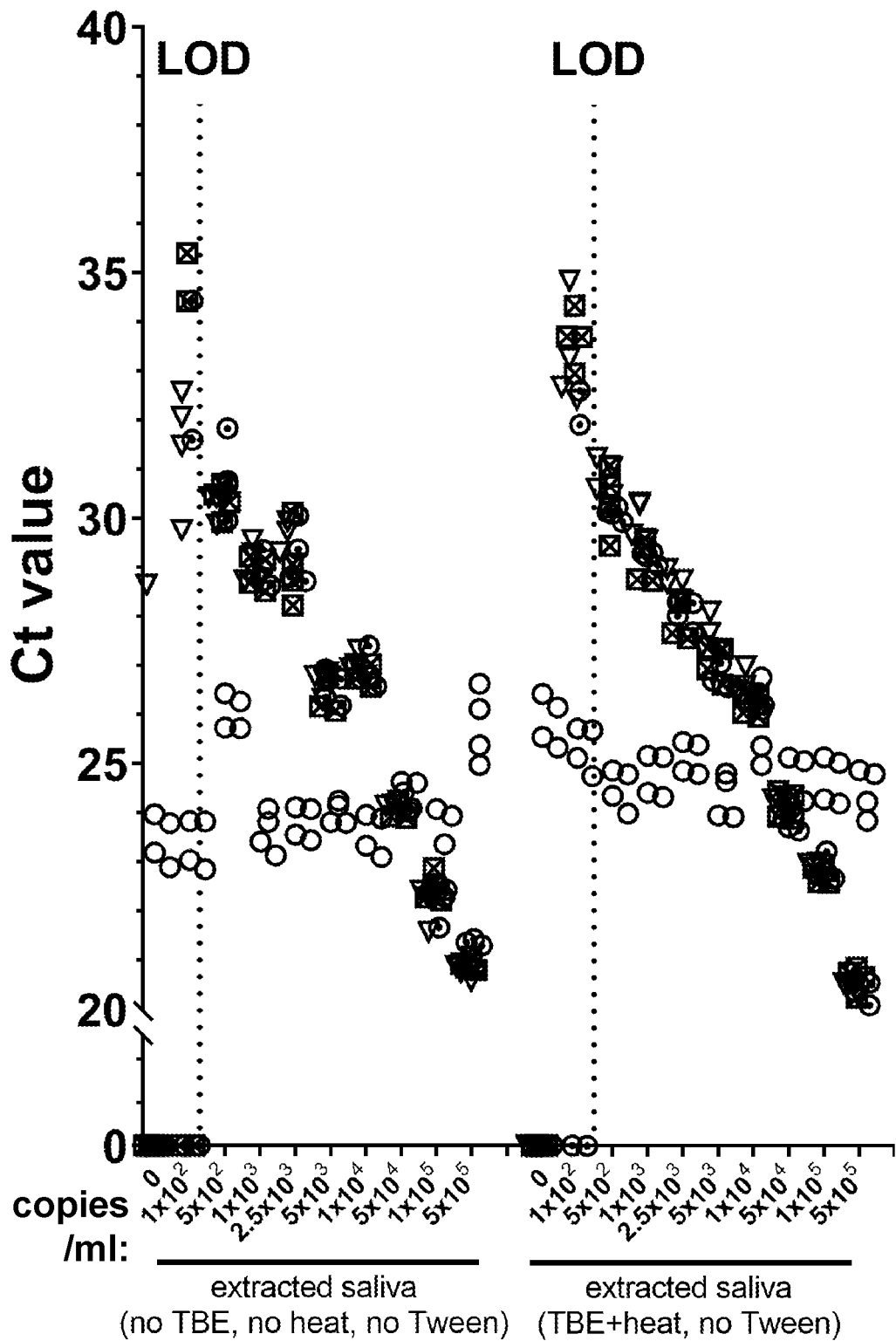
FIG. 4 illustrates the limit of detection (LOD) for assessment of SARS-CoV-2 from saliva, comparing a process utilizing RNA isolation/purification to one that bypasses RNA isolation/purification. γ-irradiated SARS-CoV-2 was spiked into fresh human saliva (SARS-CoV-2 negative), with or without TBE buffer (1×) at $1.0 \times 10^2$, $5.0 \times 10^2$, $1.0 \times 10^3$, $2.5 \times 10^3$, $5.0 \times 10^3$, $1.0 \times 10^4$, $5.0 \times 10^4$, $1.0 \times 10^5$, and $5.0 \times 10^5$ viral copies/mL. Samples were incubated at 95° C. for 30 min, then combined with or without Tween 20 (0.5%). All saliva samples were spiked with purified MS2 bacteriophage (1:40 MS2:sample) as an internal control. Virus-spiked saliva samples were either processed for RNA extraction followed by RT-qPCR (purified RNA), or directly analyzed by RT-qPCR (direct saliva). All samples, including a positive control (pos; SARS-CoV-2 positive control, $5.0 \times 10^3$ copies/mL, no MS2) and a negative control (neg; water, no MS2) were analyzed by RT-qPCR, in triplicate, for SARS-CoV-2 ORF1ab (open triangle), N-gene (open square), and S-gene (circle with inner dot), and MS2 (open circle). Undetermined Ct values are plotted at 0. The limit of detection (LOD) is indicated by the dotted vertical line.
Figure 4:
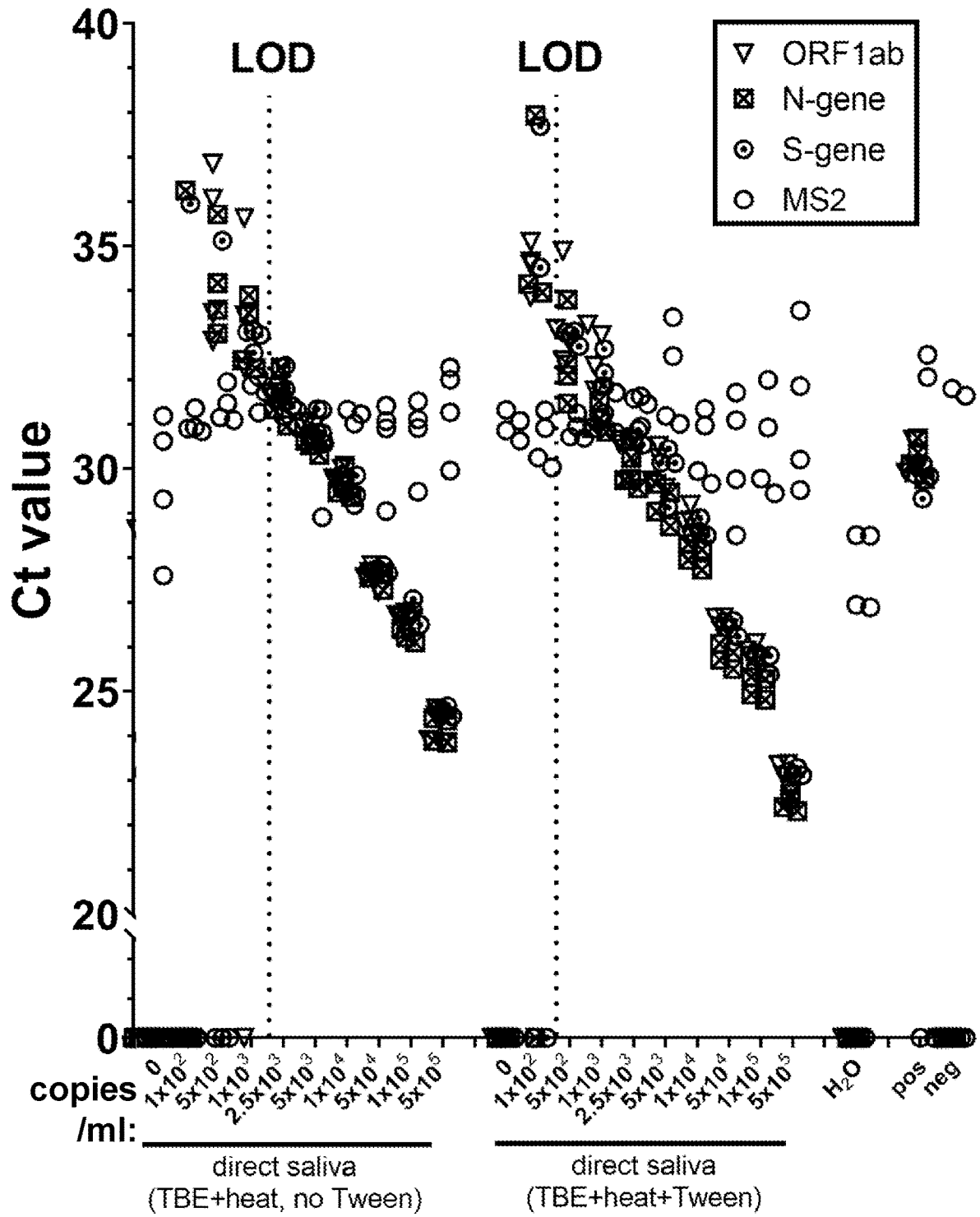
Figure 10:
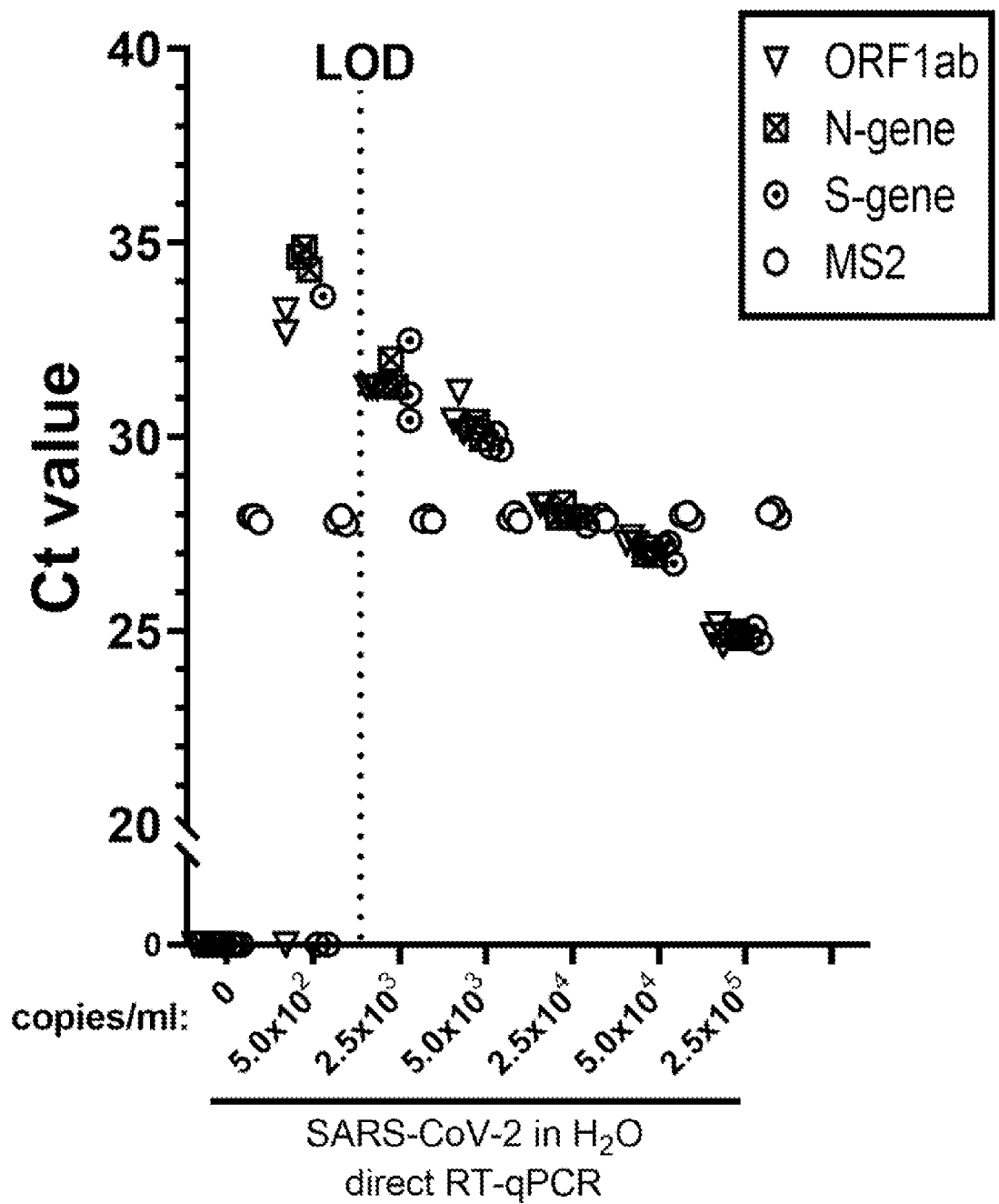
FIG. 10 illustrates the limit of detection optimization. Heat-inactivated SARS-CoV-2 was spiked into fresh human saliva (SARS-CoV-2 negative) in 0.5×TE or water at $5.0 \times 10^2$, $2.5 \times 10^3$, $5.0 \times 10^3$, $2.5 \times 10^4$, $5.0 \times 10^4$, and $2.5 \times 10^5$ viral copies/mL. Samples were incubated at 95° C. for 30 min. All samples were spiked with purified MS2 bacteriophage (1:40 MS2:sample) as an internal control. Virus-spiked samples were either processed for RNA extraction using a commercially available kit (MagMAX), or directly analyzed by RT-qPCR (direct saliva). All samples, including a positive control (pos; SARS-CoV-2 positive control, 5.0x103 copies/mL, no MS2) and a negative control (neg; water, no MS2) were analyzed by RT-qPCR, in triplicate, for SARS-CoV-2 ORF1ab (open triangle), N-gene (open square), and S-gene (circle with inner dot), and MS2 (open circle). Undetermined Ct values are plotted at 0. The limit of detection (LOD) is indicated by the vertical dotted line.
Figure 10:
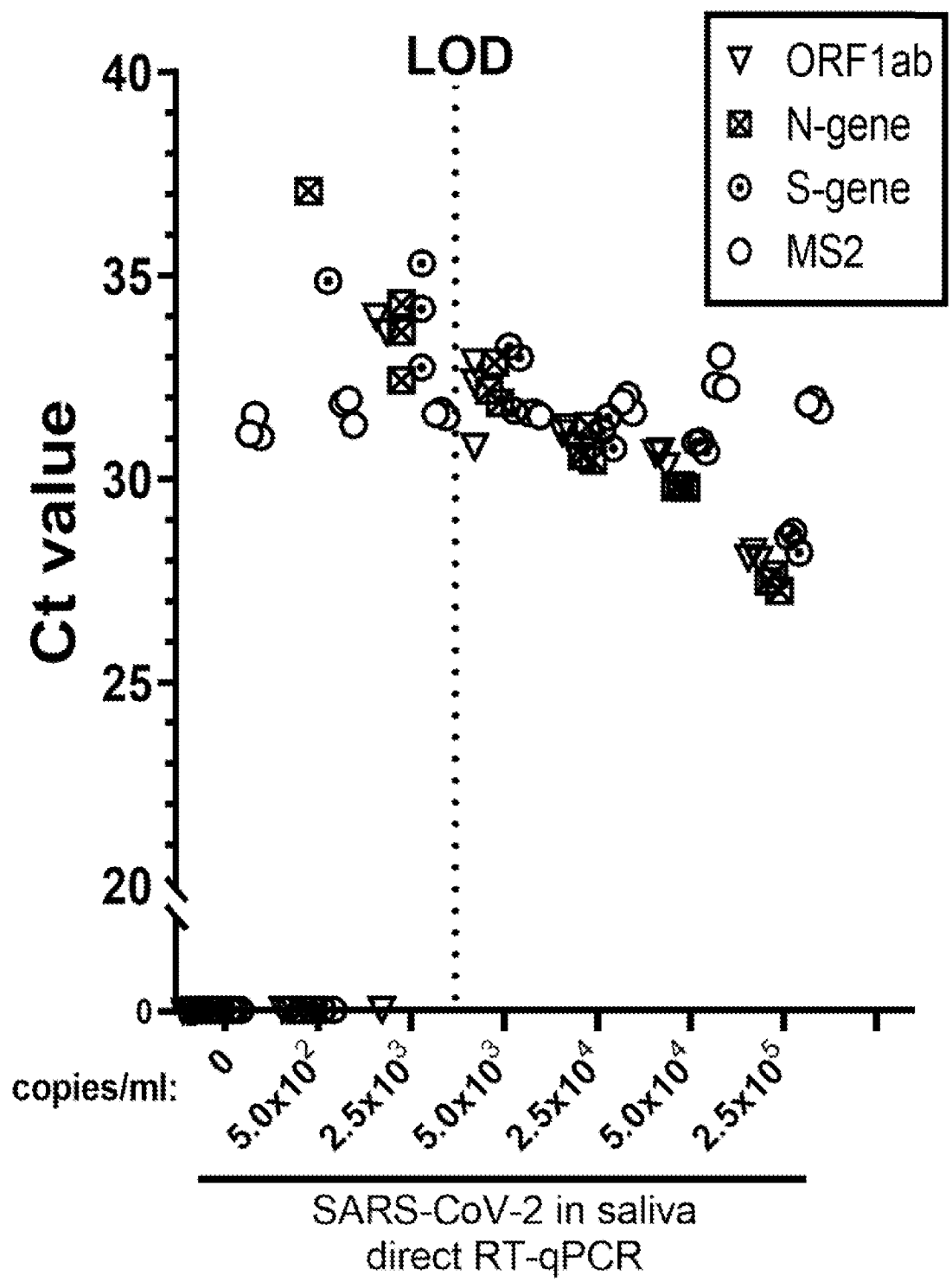
Figure 10:
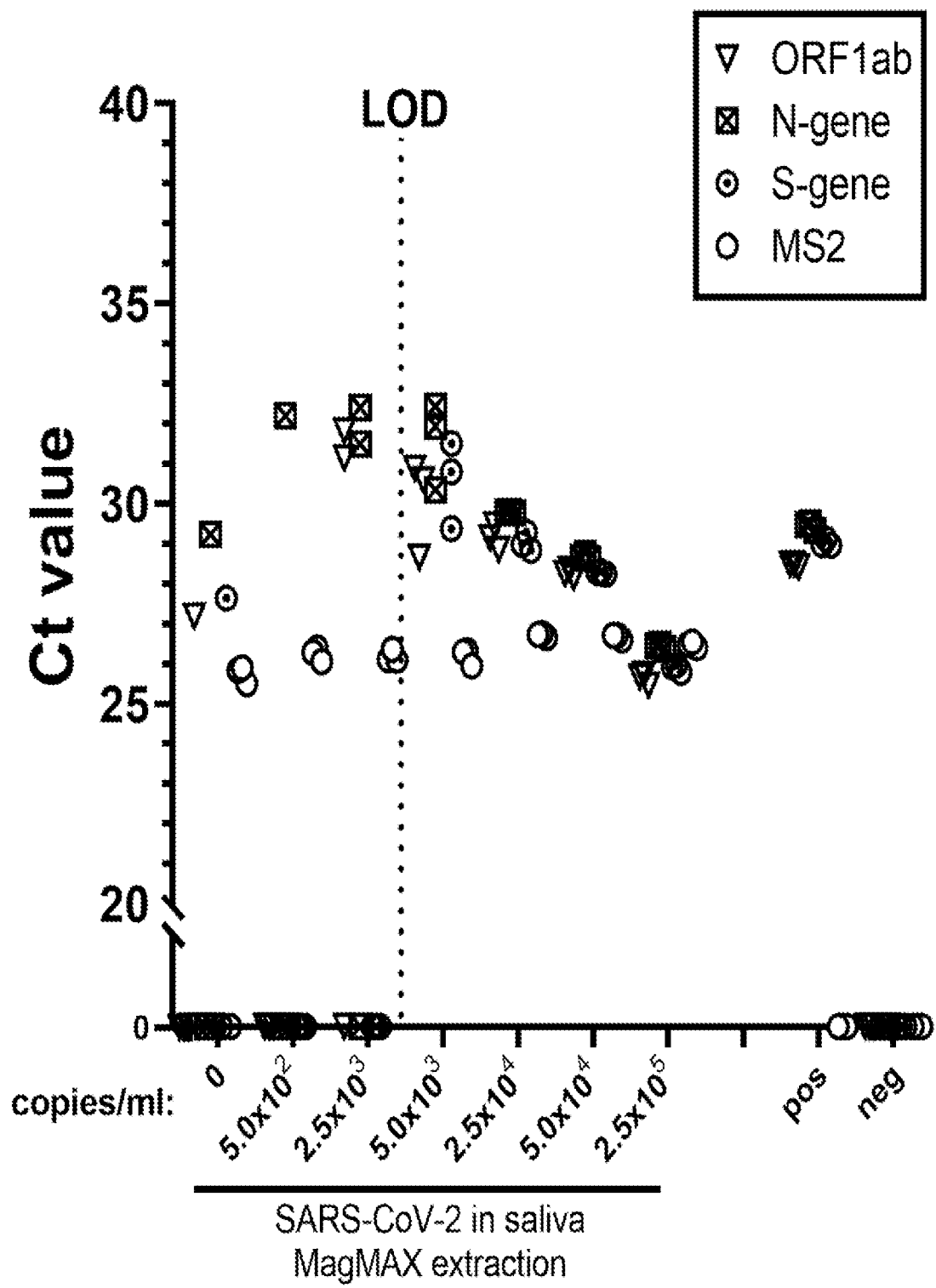

To determine the LOD for this new direct protocol (saliva→RT-qPCR), a side-by-side comparison was conducted of intact, γ-irradiated SARS-CoV-2 spiked into fresh human saliva compared to a process that includes RNA isolation/purification. As shown in FIG. 4, comparable LOD measurements were observed, with LOD of ~500 viral copies/mL for both the direct process with addition of Tween 20 and TBE buffer, and the process using RNA purification. Similar results were observed with heat-inactivated SARS-CoV-2, whereby the LOD was measured to be 5000 viral copies/mL for both RNA extraction of saliva samples and direct saliva-to-RT-qPCR, with greater detection if the virus was directly analyzed in water (FIG. 10).

Figure 11:
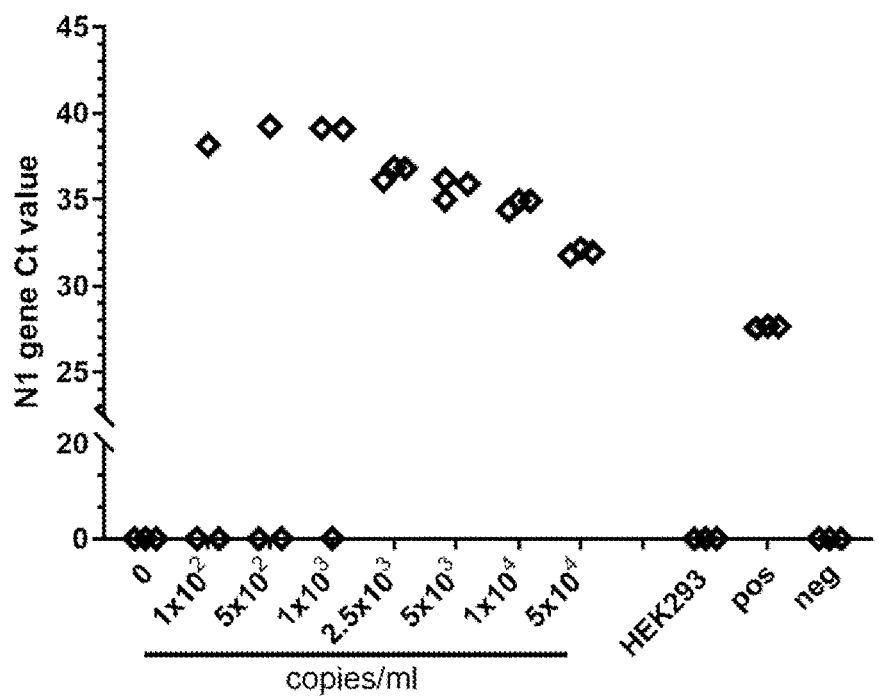
FIG. 11 illustrates the LOD of direct saliva-to-RT-qPCR SARS-CoV-2 detection using CDC-approved primers and probes. Heat-inactivated (a, b, c) and γ-irradiated (d, e, f) SARS-CoV-2 was spiked into fresh human saliva (SARS-CoV-2 negative) in 1× Tris-Borate-EDTA buffer (TBE) at $1.0 \times 10^2$, $5.0 \times 10^2$, $1.0 \times 10^3$, $2.5 \times 10^3$, $5.0 \times 10^3$, $1.0 \times 10^4$, and $5.0 \times 10^4$ viral copies/mL. Samples were incubated at 95° C. for 30 min. Virus-spiked saliva samples, a positive control (pos; SARS-CoV-2 positive control, $5.0 \times 10^3$ copies/mL) and a negative control (neg; water) were directly analyzed by RT-qPCR, in triplicate, for SARS-CoV-2 N1 gene (a, d) and N2 gene (b, e), and the human RP gene (c, f). Undetermined Ct values are plotted at 0.
Figure 11:
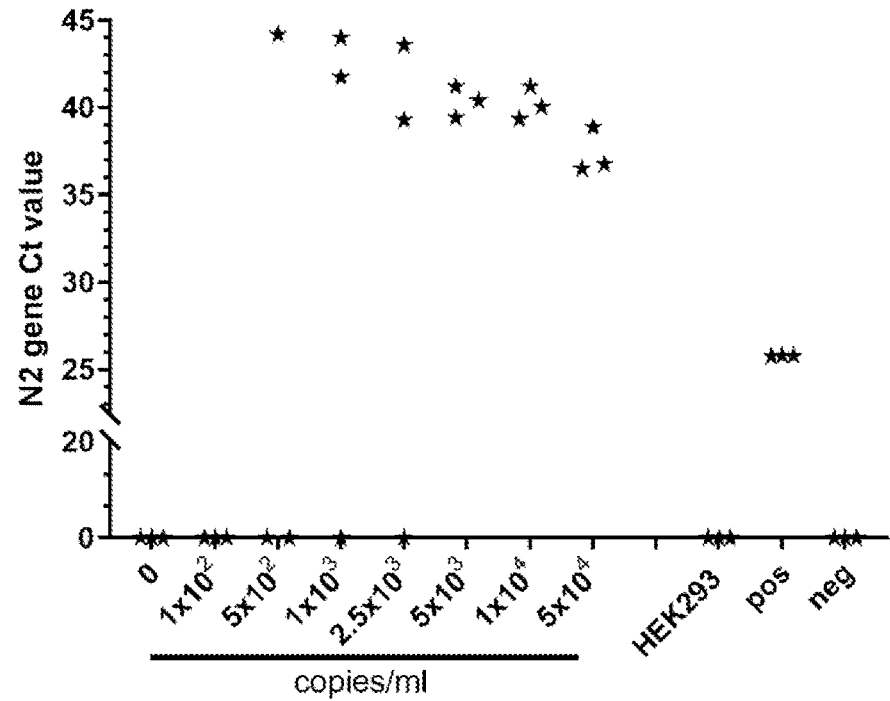
Figure 11:
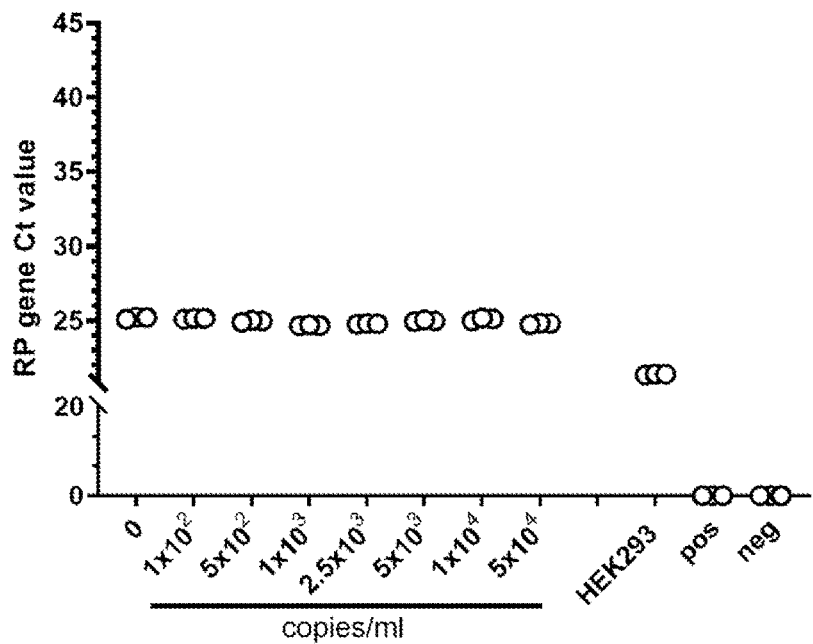
Figure 11:
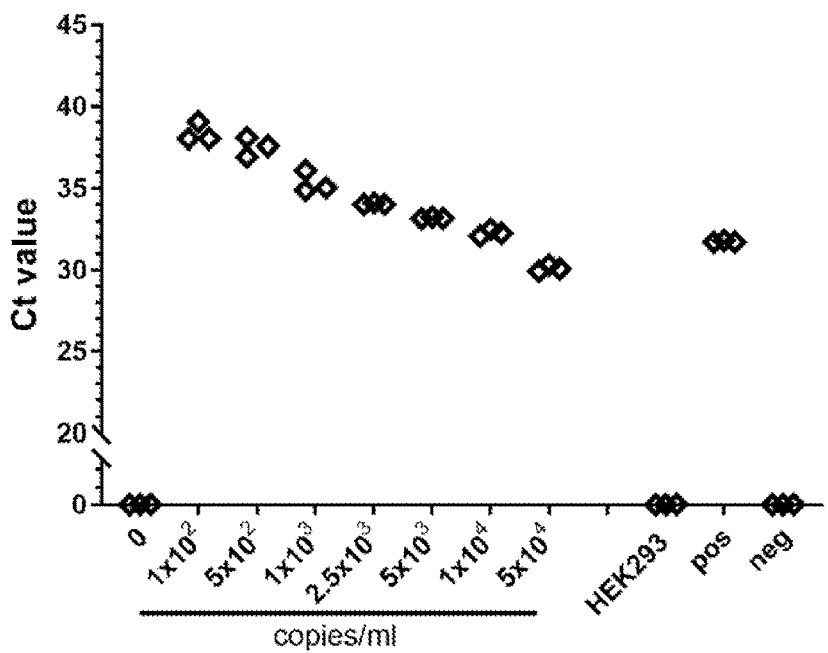
Figure 11:
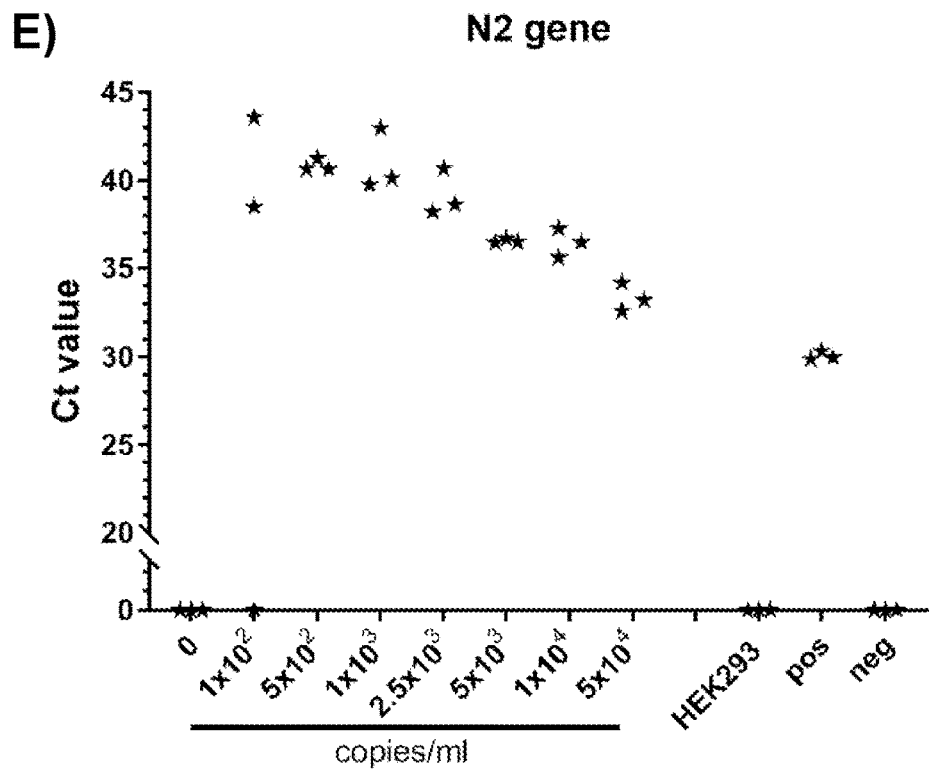
Figure 11:
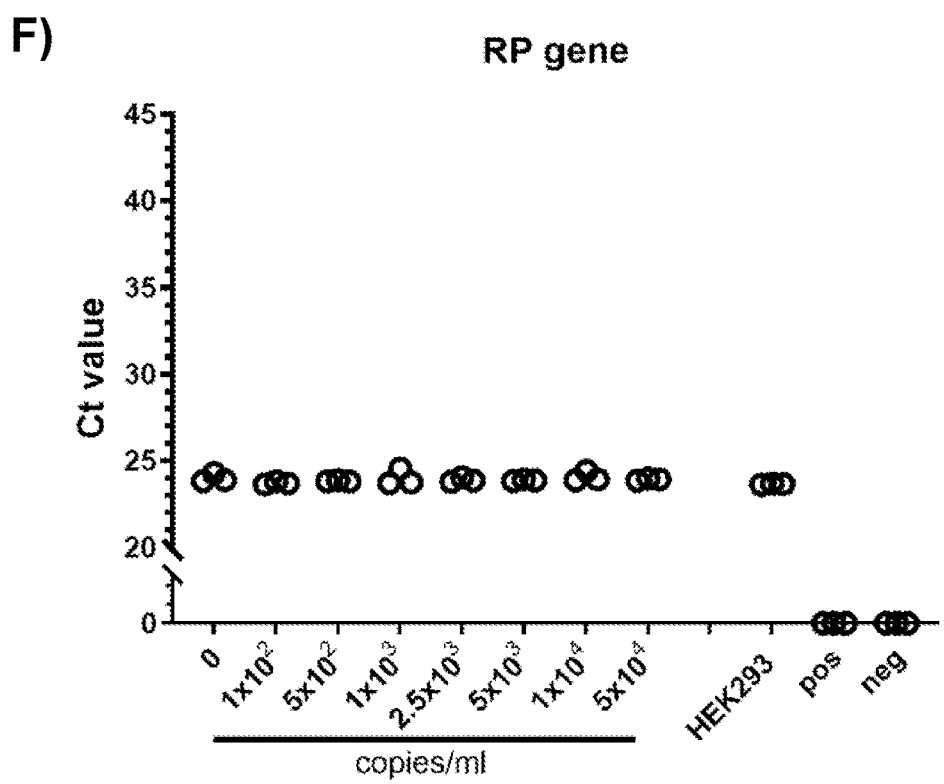

As the TaqPath/MasterMix RT-qPCR reagents from ThermoFisher provide the necessary specificity for SARS-CoV-2 detection in a simplified workflow, this system was utilized for all the experiments described above. However, we have also assessed the Centers for Disease Control and Prevention (CDC)-approved primers and probes for SARS-CoV-2 N1 and N2 genes, and the human RNase P (RP) gene control in this direct saliva-to-RT-qPCR protocol, and the results show that these primers give comparable LOD values, with 5000 viral copies/mL using heat-inactivated SARS-CoV-2, and 500 viral copies/mL using γ-irradiated SARS-CoV-2 (FIG. 11).

These findings further illustrate that our optimized protocol may be used with comparable detection across multiple analytical platforms. Altogether, these findings indicate that the optimized protocol (heat treatment of saliva samples at 95° C. for 30 min/addition of TBE buffer and Tween 20) yields a LOD that is comparable to reported clinical viral shedding concentrations in oral fluid, thus emphasizing the translatability of the protocol to detecting SARS-CoV-2 in patient samples.

Sample Handling Optimization.

Figure 12:
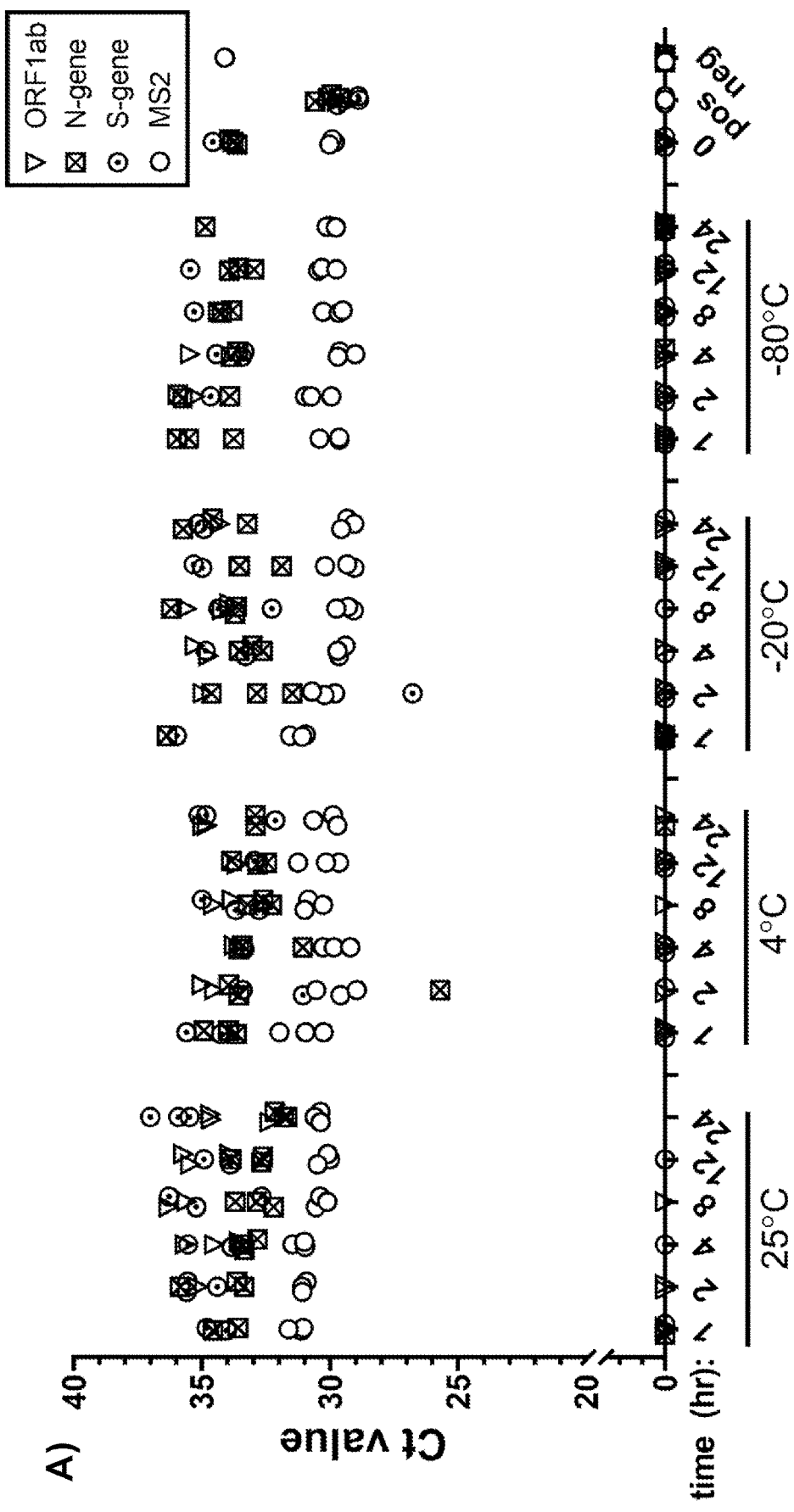
FIG. 12 illustrates the stability of saliva samples. (A) γ-irradiated SARS-CoV-2 ($1.0 \times 10^4$ viral copies/mL) was spiked into fresh human saliva (SARS-CoV-2 negative) and combined with TBE buffer 1:1 to a final working concentration of 1×. Samples (0.5 mL in 50 mL conical tubes) were stored at 25° C. (ambient temperature), 4° C., −20° C., or −80° C. for 1, 2, 4, 8, 12, and 24 hours. Following storage, samples were incubated in a hot water bath at 95° C. for 30 min. All saliva samples were spiked with purified MS2 bacteriophage (1:40 MS2:sample) as an internal control. Virus-spiked saliva samples stored under different conditions, a freshly prepared virus-spiked saliva sample (0 hr), a positive control (pos; SARS-CoV-2 positive control, $5.0 \times 10^3$ copies/mL, no MS2) and a negative control (neg; water, no MS2) were directly analyzed by RT-qPCR, in triplicate, for SARS-CoV-2 ORF1ab (open triangle), N-gene (open square), and S-gene (circle with inner dot), and MS2 (open circle). Undetermined Ct values are plotted at 0. (B) Saliva samples could be stored at room temperature for at least 7 days prior to heating and analysis without loss of sensitivity. Saliva from a SARS-CoV-2 negative subject was collected in 50 mL conical tubes. Sample was divided into sets of aliquots (one set for the negative samples and one for the positive sample). The positive samples were created by spiking the saliva with γ-irradiated SARS-CoV-2 at $5.0 \times 10^3$ viral copies/mL. Samples were further split into smaller groups for storage at either room temperature (25° C.) or at 4° C. at different time points. Following the incubation period, all samples were processed using the covidSHIELD assay, and together with a positive control (pos; SARS-CoV-2 positive control, $5.0 \times 10^3$ copies/mL) and a negative control (neg; water), were directly analyzed by RT-qPCR in triplicates for SARS-CoV-2 ORF1ab (triangle), N-gene (square), and S-gene (dotted circle), and MS2 (open circle). MS2 bacteriophage was added to the PCR reaction mix as internal control. Undetermined Ct values are plotted as ND. Saliva stability experiment prior to heat inactivation was repeated twice.
Figure 12:
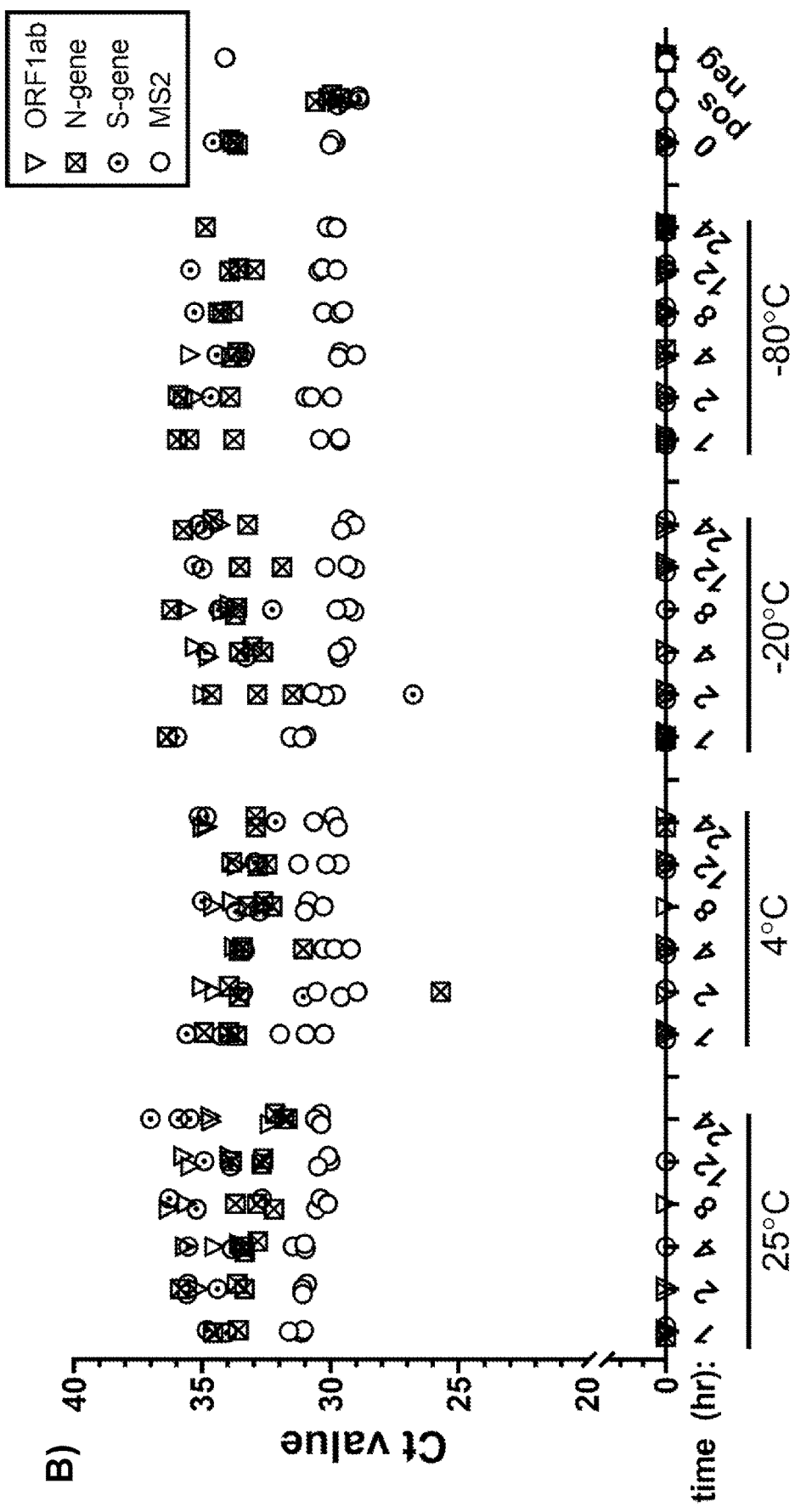

In preparation for clinical samples and real-world testing, we first evaluated the ability to detect spiked inactivated virus in samples that were stored at varying temperatures (ambient (25° C.), 4° C., −20° C., and −80° C.), for varying lengths of time (≤24 hrs). Although virus was detectable in all storage conditions (>1 gene replicate detected below a Ct value of 40), some increased variability between individual gene replicates and loss of signal was observed, indicating that prolonged storage and freeze/thaw cycles may affect reproducibility of virus detection within a given sample (FIG. 12). Therefore, in order to maximize efficiency, reproducibility, and consistency of testing, it is recommended to process samples within several hours of collection, and maintain samples at −80° C. for long-term (>24 hours), to limit microbial growth and degradation of samples.

Figure 13:
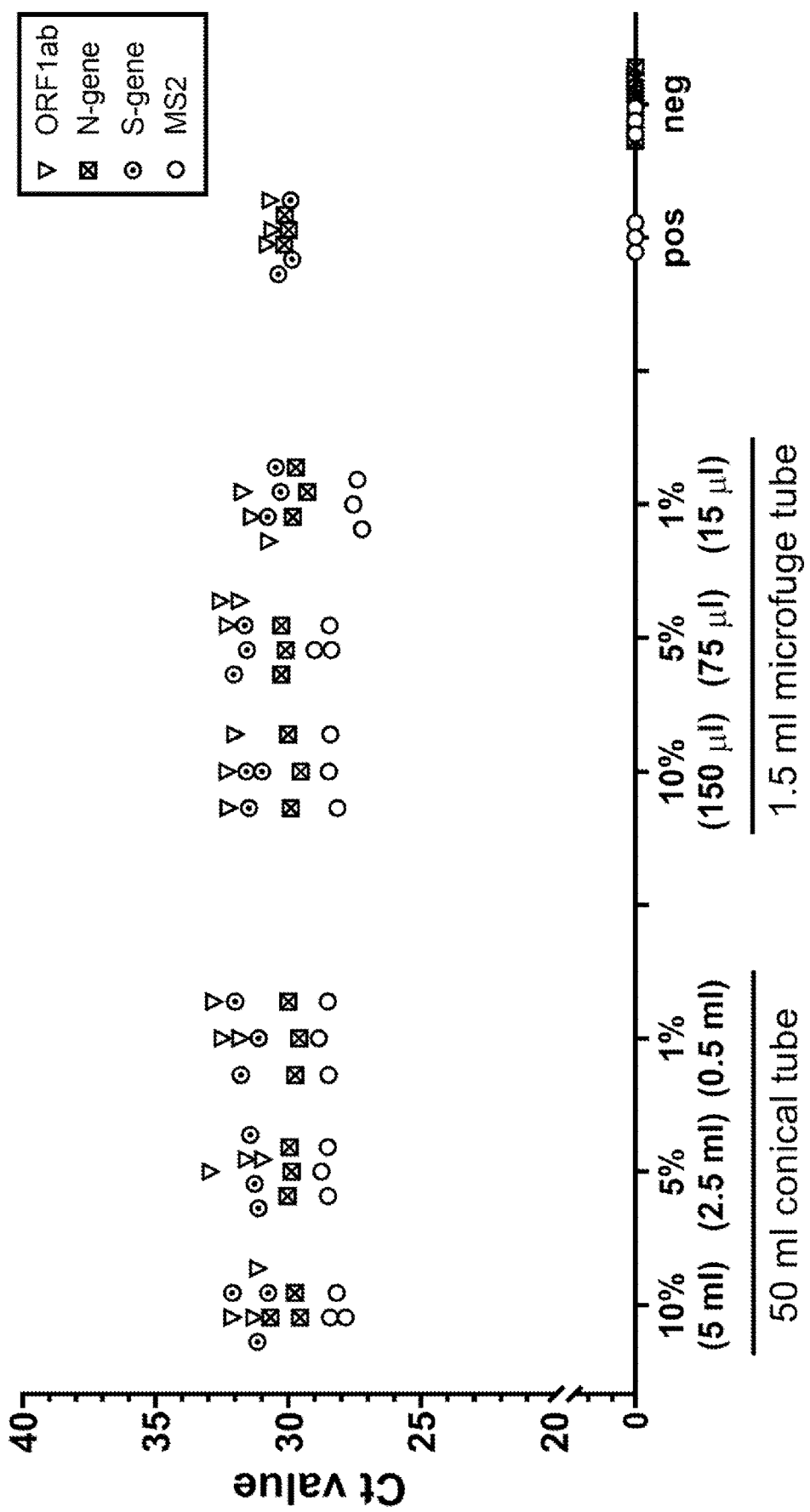
FIG. 13 illustrates the effect of sample volume on SARS-CoV-2 detection. γ-irradiated SARS-CoV-2 ($1.0 \times 10^4$ viral copies/mL) was spiked into fresh human saliva (SARS-CoV-2 negative) and combined with TBE buffer 1:1 at a final working concentration of 1×. The sample was distributed into either 50 mL conical or 1.5 mL microfuge tubes, at either 10% (5 mL in 50 mL conical, 150 μL in 1.5 ml microfuge), 5% (2.5 mL in 50 ml conical, 75 μL in 1.5 ml microfuge), or 1% (0.5 mL in 50 mL conical, 15 μL in 1.5 mL microfuge) the vessel storage capacity. Samples were incubated in a hot water bath at 95° C. for 30 min. All saliva samples were spiked with purified MS2 bacteriophage (1:40 MS2:sample) as an internal control. Virus-spiked saliva samples, a positive control (pos; SARS-CoV-2 positive control, $5.0 \times 10^3$ copies/mL, no MS2) and a negative control (neg; water, no MS2) were directly analyzed by RT-qPCR, in triplicate, for SARS-CoV-2 ORF1ab (open triangle), N-gene (open square), and S-gene (circle with inner dot), and MS2 (open circle). Undetermined Ct values are plotted at 0.

Next, evaluation was made of the effect of sample volume in the saliva collection vessels (50 mL conical tubes) on viral detection, after heating at 95° C. for 30 min in a hot water bath, due to concerns of evaporation of smaller samples and incomplete heating of larger samples. No appreciable difference was observed across the anticipated range of clinical saliva sample volumes (0.5-5 mL), indicating that sample volume does not impact virus detection (FIG. 13). Furthermore, if samples are transferred to smaller vessels for more efficient long-term cold storage (1.5 mL microcentrifuge tubes), no appreciable differences in virus detection between different volumes is anticipated (FIG. 13).

Figure 14:
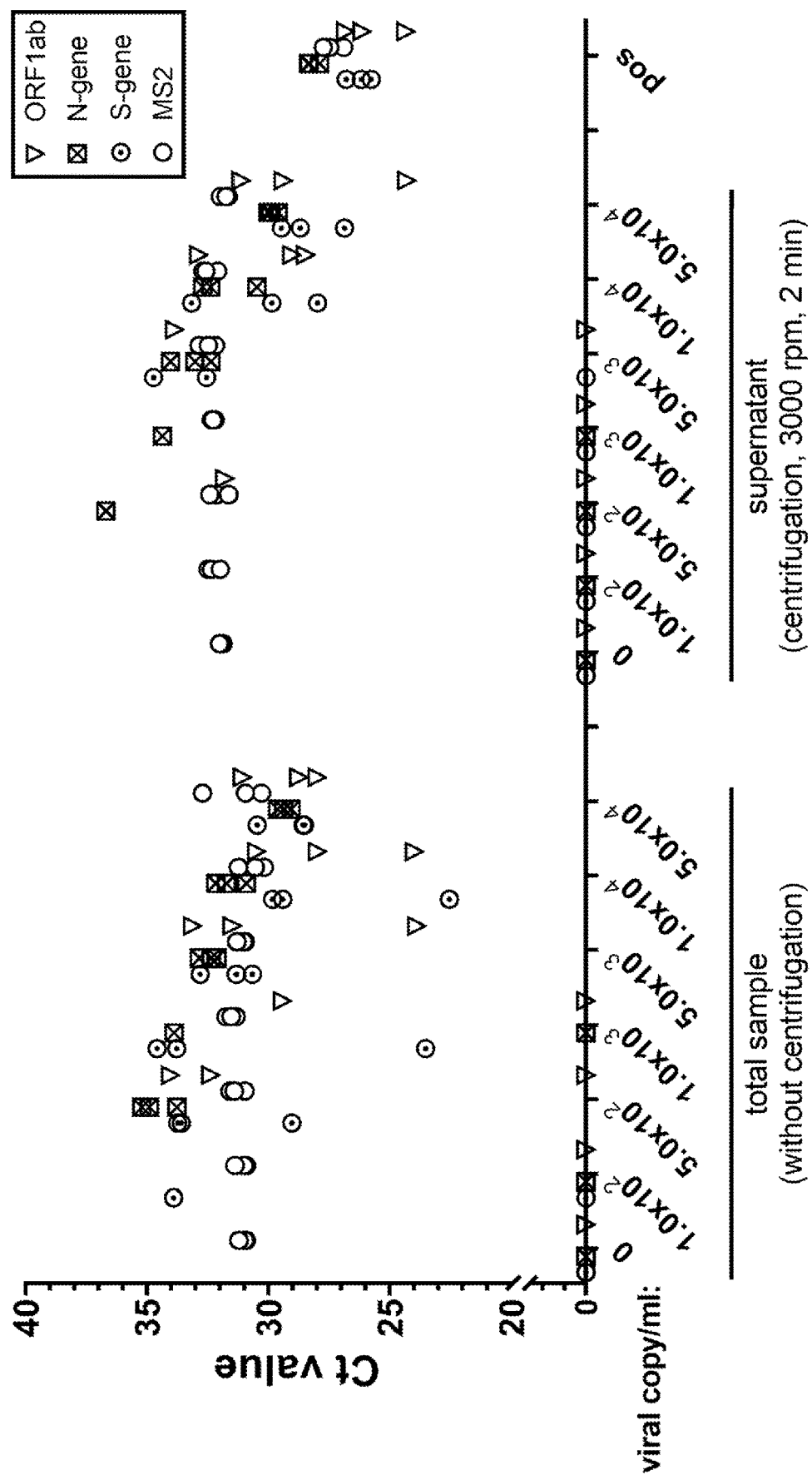
FIG. 14 illustrates the effect of centrifugation on SARS-CoV-2 detection. Heat-inactivated SARS-CoV-2 ($1.0 \times 10^2$, $5.0 \times 10^2$, $1.0 \times 10^3$, $5.0 \times 10^3$, $1.0 \times 10^4$, and $5.0 \times 10^4$ viral copies/mL) was spiked into fresh human saliva (SARS-CoV-2 negative) and combined with TBE buffer 1:1 at a final working concentration of 1×. Samples were heat treated at 95° C. for 30 min, then treated with or without centrifugation at 3000 rpm for 2 min. All saliva samples were spiked with purified MS2 bacteriophage (1:40 MS2:sample) as an internal control. Virus-spiked saliva samples, centrifugation supernatants, a positive control (pos; SARS-CoV-2 positive control, $5.0 \times 10^3$ copies/mL) and a negative control (neg; water) were directly analyzed by RT-qPCR, in triplicate, for SARS-CoV-2 ORF1ab (open triangle), N-gene (open square), and S-gene (circle with dot), and MS2 (open circle). Undetermined Ct values are plotted at 0.

Finally, as clinical saliva samples can sometimes contain particulates, we next evaluated whether removal of the particulates via centrifugation affected viral detection (FIG. 14). Notably, if samples were centrifuged, with the resultant supernatant being used for direct RT-qPCR, the LOD was approximately 10-fold worse, with fewer individual gene replicates being detected at lower viral copy numbers (FIG. 14). Therefore, we recommend avoiding centrifugation of samples if possible. Altogether, these findings suggest that (1) saliva samples are stable under varying storage conditions, (2) the volume of sample heated with collection vessels does not affect viral detection, and (3) centrifugation of samples should be avoided for direct saliva-to-RT-qPCR testing of SARS-CoV-2.

LOD Reproducibility.

Figure 5:
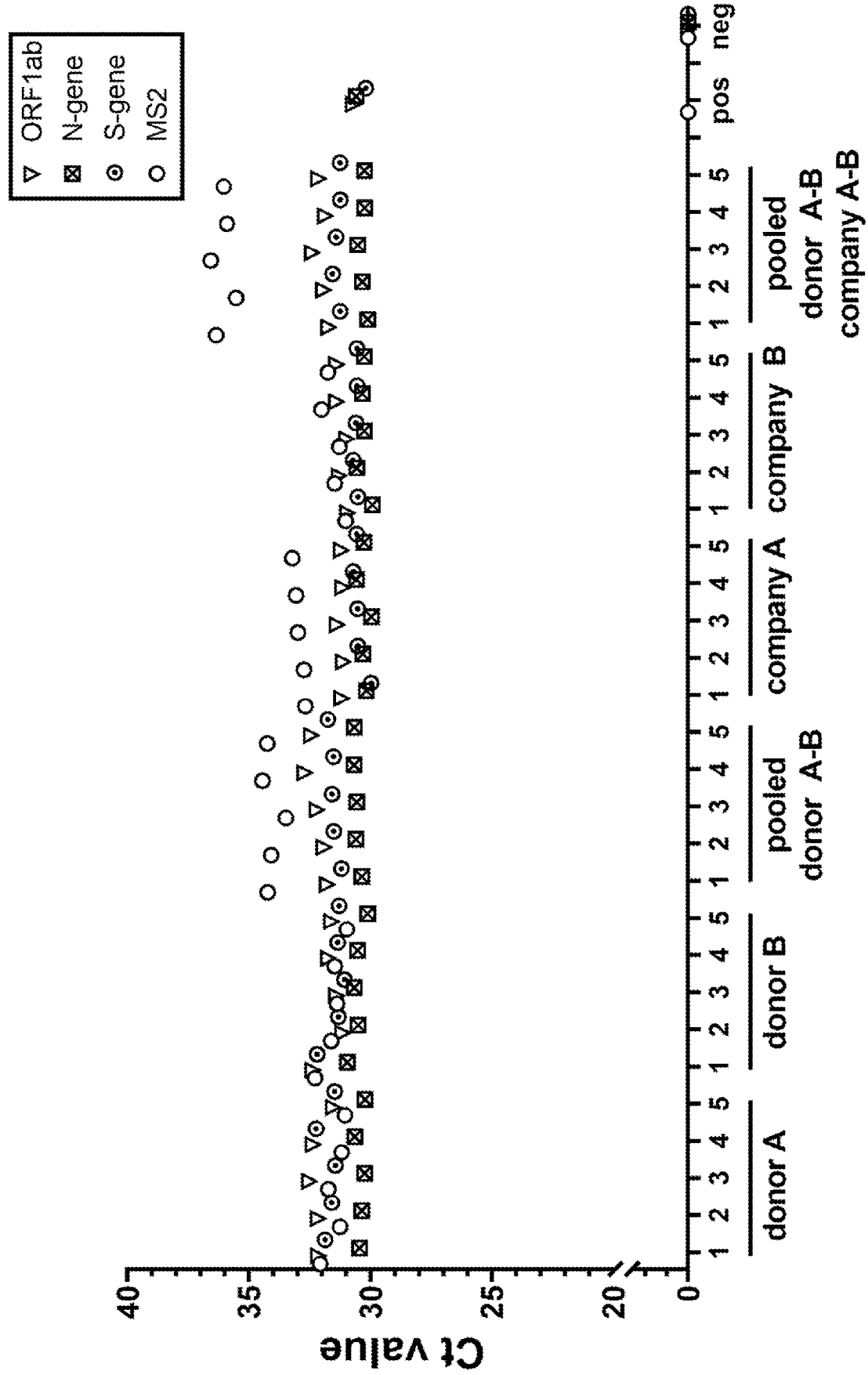
FIG. 5 illustrates the limit of detection (LOD) reproducibility. γ-irradiated SARS-CoV-2 was spiked into human saliva (SARS-CoV-2 negative), sourced fresh from two healthy donors, and purchased from two companies, in 1×TBE buffer at $1.0 \times 10^3$ viral copies/mL. Samples were incubated at 95° C. for 30 min, then Tween 20 was added to a final concentration of 0.5%. All saliva samples were spiked with purified MS2 bacteriophage (1:40 MS2:sample) as an internal control. Virus-spiked saliva samples were directly analyzed by RT-qPCR (direct saliva). All samples, including a positive control (pos; SARS-CoV-2 positive control, $5.0 \times 10^3$ copies/mL, no MS2) and a negative control (neg; water, no MS2) were analyzed by RT-qPCR, in replicates of 5, for SARS-CoV-2 ORF1ab (open triangle), N-gene (open square), and S-gene (circle with inner dot), and MS2 (open circle). Undetermined Ct values are plotted at 0.
Figure 15:
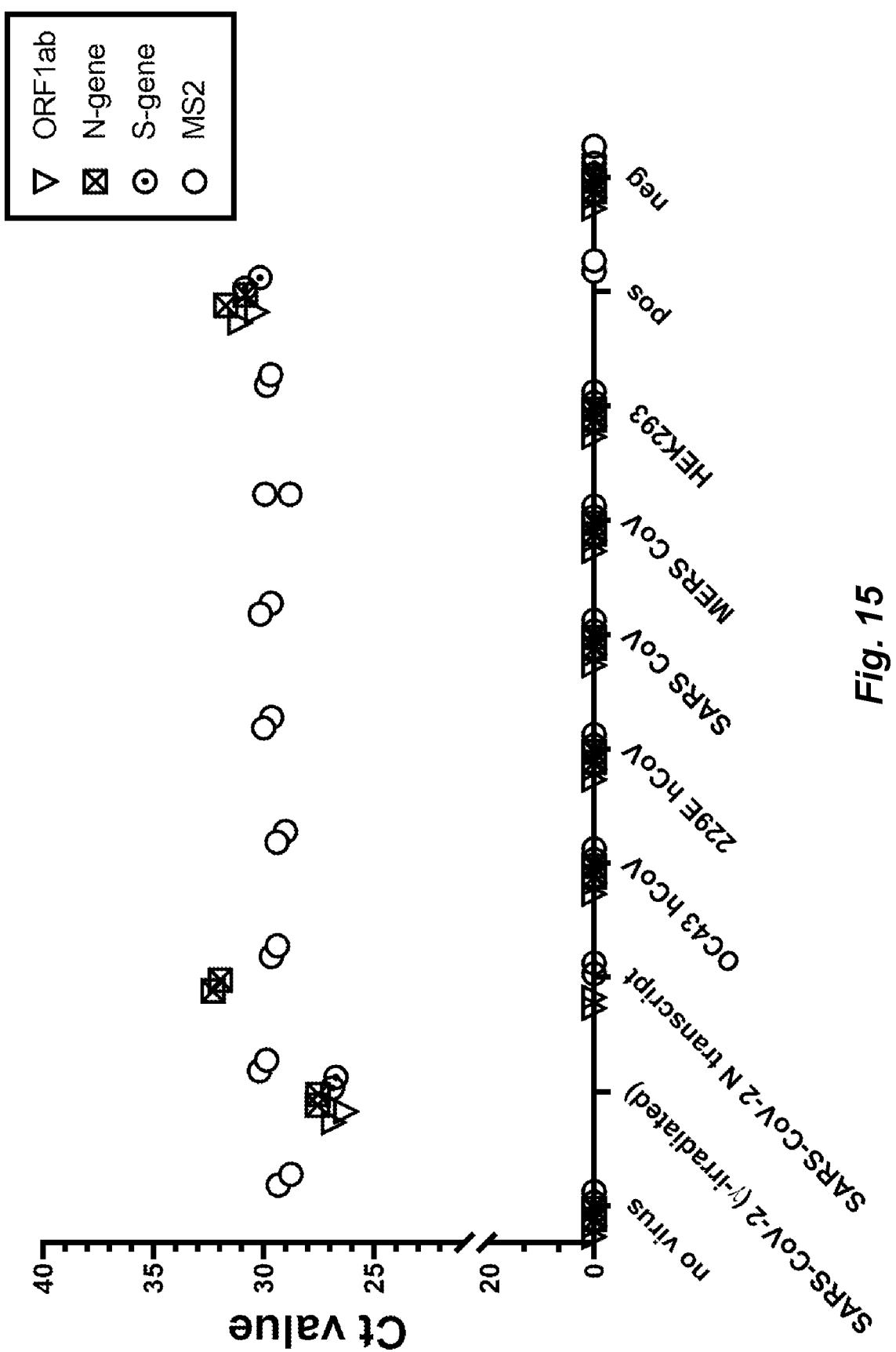
FIG. 15 illustrates the specificity of SARS-CoV-2 detection system. Commercially available saliva (Lee Biosciences and Innovative Research) was combined in equal proportions, diluted 1:1 with 2×TBE buffer, and spiked $1.0 \times 10^5$ viral copies/mL of SARS-CoV-2 (γ-irradiated virus or synthetic N-transcript RNA), human coronaviruses (229E, OC43), SARS and MERS synthetic RNA, and human RNA (purified from HEK 293 cells). Samples were heat treated at 95° C. for 30 minutes. All saliva samples were spiked with purified MS2 bacteriophage (1:40 MS2:sample) as an internal control. Virus-spiked saliva samples, a positive control (pos; SARS-CoV-2 positive control, $5.0 \times 10^3$ copies/mL) and a negative control (neg; water, no MS2) were directly analyzed by RT-qPCR, in triplicate, for SARS-CoV-2 ORF1ab (open triangle), N-gene (open square), and S-gene (circle with inner dot), and MS2 (open circle). Undetermined Ct values are plotted at 0.

In order to evaluate the robustness of the optimized direct saliva-to-RT-qPCR approach, the LOD of 1000 SARS-CoV-2 viral copies/mL was measured in 30 independent replicate samples (FIG. 5). γ-irradiated SARS-CoV-2 was spiked into fresh saliva from two healthy donors, and two commercially available saliva sources. Across all replicates, these samples with 1000 viral copies/mL were consistently detected (all three viral genes), further testifying to the ability of direct saliva-to-RT-qPCR to detect SARS-CoV-2. In order to validate the specificity of our detection system to SARS-CoV-2, saliva was spiked with or without SARS-CoV-2 (γ-irradiated virus, synthetic N-transcript), two other human coronaviruses (OC43, 229E), SARS and MERS synthetic RNA, and human RNA (extracted from HEK 293 cells). Among these samples, SARS-CoV-2 genes were only detected in the positive control, and SARS-CoV-2 samples, further supporting the specificity of the detection platform for SARS-CoV-2 (FIG. 15).

Clinical Validation of Direct Saliva-to-RT-qPCR for Diagnosis of SARS-CoV-2.

Our findings support an optimized SARS-CoV-2 diagnostic approach that increases accessibility to testing by using saliva (rather than NP swabs) and eliminates the need for RNA extraction (thus saving time and resources). We next sought to assess our protocol with clinical samples. Although the changes in viral load in the NP cavity and in saliva over time are unknown, there is reason to believe they are different, so exact concordance between the two samples might not be expected; detection in saliva can provide complementary information to that in the NP cavity.

To evaluate the ability of the direct saliva-to-RT-qPCR approach to detect SARS-CoV-2 in clinical patient specimens, saliva was collected contemporaneously with NP swabs from 100 individuals using the following protocol: After saliva collection, TE was added at a 1:1 ratio, and samples were frozen for over a week before processing. For the evaluation, samples were thawed, 10×TBE buffer was added to a final concentration of 1×, heated at 95° C. for 30 min, cooled to room temperature, and Tween 20 was added to a final concentration of 0.5%, followed by direct RT-qPCR. Given biological complexity in clinical samples, variabilities in signal detection based on viral load and gene target length (ORF1ab>S>N) may occur; therefore, a given result was interpreted as positive if one or more gene targets were detected, and negative if no gene targets were detected. Furthermore, a result was considered valid if all gene targets were detected in the SARS-CoV-2 positive control and no gene targets were detected in the negative control.

A notable power in the context of a multiplex system is the ability to evaluate three independent viral genes in a single reaction, rather than relying upon multiple probes across different reactions for a single viral gene (as is used in other systems). One of the benefits of saliva-based testing is the possibility of frequent and easy retesting of samples and of individuals, and as such duplicate testing (testing of the same saliva sample two different times) was utilized for this study.

Figure 6:
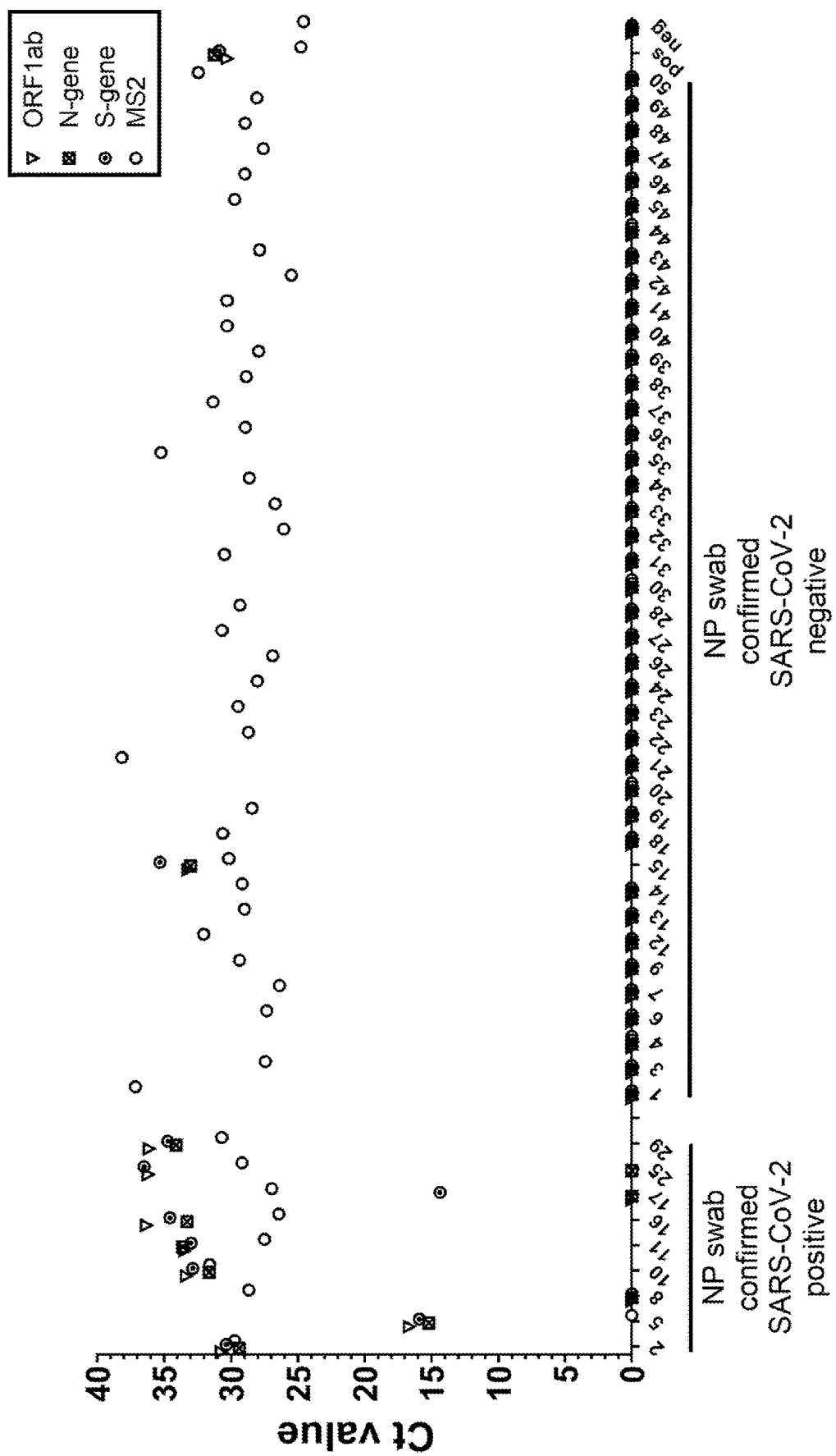
FIG. 6 illustrates the assessment of clinical samples. Saliva samples from 9 SARS-CoV-2 positive and 91 SARS-CoV-2 negative patients (as judged by NP swabs in VTM with RNA extraction) had TE buffer added to them (at a 1:1 ratio) and were frozen for over a week. Upon thawing, 10×TBE buffer was added to the samples at a final concentration of 1×, heated at 95° C. for 30 min, cooled to room temperature, and Tween 20 was added to a final concentration of 0.5%. All saliva samples were spiked with purified MS2 bacteriophage (1:40 MS2:sample) as an internal control. Saliva samples were directly analyzed by RT-qPCR (direct saliva). All samples, including
a positive control (pos; SARS-CoV-2 positive control, $5.0 \times 10^3$ copies/mL) and a negative control (neg; water) were analyzed by RT-qPCR, in singlet, for SARS-CoV-2 ORF1ab (open triangle), N-gene (open square), and S-gene (circle with inner dot), and MS2 (open circle). Undetermined Ct values are plotted at 0.
Figure 6:
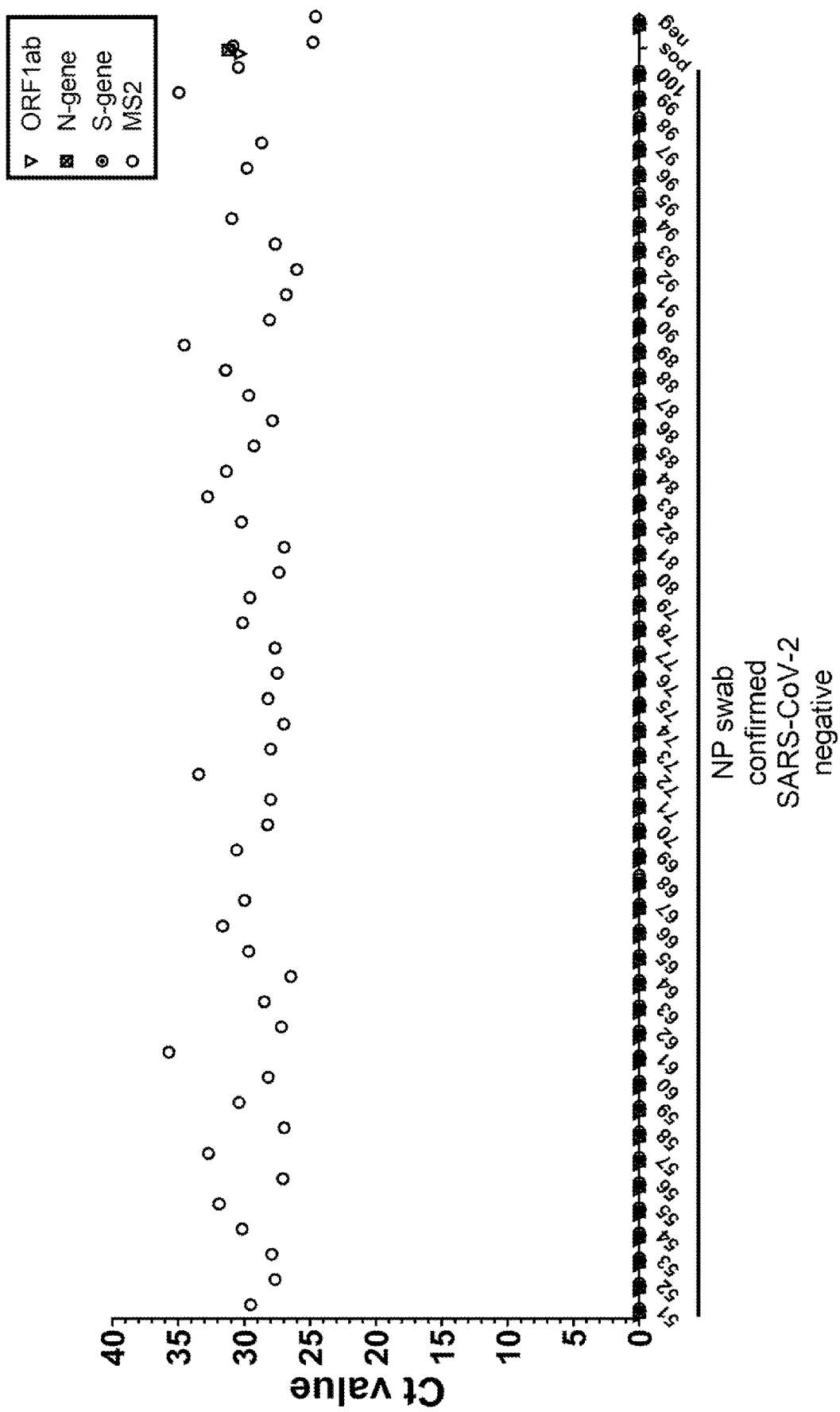

Of the 100 samples analyzed, 9 were positive for SARS-CoV-2 as assessed by NP swab, and upon duplicate testing the direct saliva-to-RT-qPCR process identified the same 9 samples as positive, with 8 of 9 saliva samples positive in both of the replicates. All 91 samples identified as negative by NP swab were also negative via saliva testing, although in one of these samples one of the duplicate runs was positive but was negative upon re-tests (FIG. 6). Even though these samples were not run under the fully optimized protocol, this initial testing of clinical samples using direct saliva-to-RT-qPCR showed excellent performance. When testing samples, a single time, it was 88.9% sensitive and 98.9% specific for SARS-CoV-2, with an 11.1% false negative and 1.1% false positive rate, and 88.9% positive and 98.9% negative predictive value. Using duplicate testing of samples, sensitivity and specificity, and positive and negative predictive values, all increased to 100%, and the false negative and positive rates decreased to 0%.

Discussion

Comparison of NP swab and saliva-based testing. When seeking to develop a SARS-CoV-2 molecular diagnostic protocol suitable for testing >10,000 individuals a day, the ease with which saliva can be collected, and the known presence of the virus in saliva makes it highly desirable as the sample medium. As a diagnostic tool, such testing has the additional advantage of making assessments directly from an oral fluid that may be culprit in transmission of SARS-CoV-2. Unfortunately, only a handful of studies have examined the viral load dynamics over time for saliva and NP swab samples. While these studies support the notion that SARS-CoV-2 tends to be at its highest level in saliva during the first week of infection, more information is needed on this important topic. In contrast, studies have shown that while live virus can no longer be cultured from patients 10 days after symptom onset, NP swabs continue to be positive after a patient is in the convalescent phase and no longer infectious. 13 As such, it is quite possible that differences observed in studies comparing SARS-CoV-2 levels in saliva and NP swabs are real, and not an artifact of different testing sensitivities; while in general concordance between the NP swab and saliva testing has been high in other studies (87%, 92%, 100%), results will likely depend on what point during infection a patient is sampled.

Direct saliva-to-RT-qPCR process, key advances and remaining limitations. The direct saliva-to-RT-qPCR method described herein, bypassing NP swabs, VTM, and RNA isolation/purification, was enabled by a handful of key discoveries. First, the time and duration of heating the saliva sample is critical. Standard protocols for heat inactivation of SARS-CoV-2 call for heating at ~60° C. for 30 minutes; while these conditions inactivate the virus, they do not allow for successful SARS-CoV-2 detection via direct RT-qPCR, likely because of the persistence of as-yet-unidentified factors in saliva that are inhibitory to RT-qPCR. Heating at 95° C. for 30 minutes inactivates these inhibitory components and allows for excellent SARS-CoV-2 detection in this direct process that bypasses RNA isolation/purification. Second, while TE buffer performs well, consistent with another report successfully using TE to extract dry NP swabs, TBE buffer provides more reliability and consistency in our direct saliva-to-RT-qPCR detection of SARS-CoV-2. Finally, the addition of the non-ionic detergent Tween-20 also helped improve detection of SARS-CoV-2, possibly by facilitating the opening of the viral capsid to allow the release of RNA to provide sufficient template for RT-qPCR detection.

Our assessment of clinical samples is very promising, especially given that these samples were not collected and processed under the optimized protocol (they were collected before our discovery of the benefits of TBE buffer and Tween 20); with these samples TE buffer was added to the sample, and they were frozen for over a week before processing. However, even under this non-optimized workflow we were able to identify all 9 NP swab positives with duplicate runs of the samples. Next steps are to perform similar head-to-head comparisons between the NP swab-based method and our optimized workflow with additional clinical samples.

Supply chain, costs, and next-generation technology. A major benefit of the simple workflow detailed herein is its ability to be adopted by any diagnostic laboratory currently using RT-qPCR in SARS-CoV-2 testing. In addition to the time savings and major logistical benefits of using saliva and bypassing RNA isolation/purification, our analysis of the costs of all reagents/disposables for this process amounts to ~$10 per test, the bulk of which are the TaqPath/MasterMix. This cost could drop further if samples are pooled before RT-qPCR. Pooling considerations will necessarily be informed by data on the expected positive rate in the population to be tested, and also the relationship between viral load and infectivity; while one recent study showed that live SARS-CoV-2 could not be cultured from samples containing less than 1,000,000 viral copies per mL, more information is needed. And, while there is no indication that TaqPath/MasterMix will be limited by the supply chain, we show that this process and workflow is also compatible with other primer sets, such as the N1 and N2 primers and probes from the CDC. In the future, development of analogous saliva-based processes that bypass RNA isolation/purification can be envisioned for alternative back-end detection technologies, such as the LAMP method, which if successful would result in an even shorter overall time from sample collection to results.

In summary, described herein is a sensitive diagnostic method for SARS-CoV-2 that is operationally simple, bypasses supply chain bottlenecks, evaluates a clinically relevant infectious fluid, is appropriate for large scale repeat testing, is cost effective, and can be readily adopted by other laboratories. Large scale SARS-CoV-2 testing will be a powerful weapon in preventing spread of this virus and helping to control the COVID-19 pandemic.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Materials and Methods

Acquisition and Processing of Clinical Samples

All clinical samples from study participants were collected in accordance with University of Illinois at Urbana-Champaign (UIUC) IBC-approved protocol number 4604 and IRB-approved protocol number 20CRU3150. Saliva in 1:1 1×TE buffer and discarded VTM samples collected from 100 adults at the Carle Foundation Hospital Drive-thru COVID-19 testing center were collected and frozen at −80° C. for over a week. Upon thawing, 10×TBE buffer was added to the samples to a final concentration of 1×, heated at 95° C. for 30 min, cooled to room temperature, and Tween 20 was added to a final concentration of 0.5%. The optimized direct saliva-to-RT-qPCR approach was compared to detection of SARS-CoV-2 from nasopharyngeal (NP) swab in VTM performed at the Carle Foundation Hospital. In all studies conducted, researchers were blinded to the results obtained from clinical RT-qPCR tests performed on NP swabs at the Carle Foundation Hospital.

Collection and Processing of Fresh Saliva from Healthy Donors

Fresh saliva was collected from healthy individuals in 50 mL conical tubes (BD Falcon) in accordance with University of Illinois at Urbana-Champaign IBC-approved protocol numbers 4604 and 4589. In some experiments, pooled saliva from healthy donors was purchased from Lee BioSolutions, Inc. (CN 991-05-P) and Innovative Research (CN IRHUSL50ML). Saliva was diluted at a 1:1 ratio with either TBE buffer (100 mM Tris-HCl pH8.0, 90 mM boric acid, and 1 mM EDTA) or TE buffer (10 mM Tris-HCl pH8.0 and 1 mM EDTA) buffer. In some experiments, Phosphate Buffered Saline (PBS), DNA/RNA Shield (Zymo Research), and SDNA-1000 (Spectrum Solutions), were also tested at final working concentrations of 2×, 1.5×, 1×, and 0.5×. Known amounts of the SARS-CoV-2 inactivated virus (BEI) were spiked into saliva samples. Samples were incubated in a hot water bath at 95° C. for 30 min. All saliva samples were spiked with purified MS2 bacteriophage (1:40 MS2:sample) as an internal control. In some experiments, RNA extraction was performed on 200 µL saliva (+/−virus) using MagMax Viral/Pathogen II Nucleic Acid Isolation Kit (Applied Biosciences CN A48383) following the manufacturer's protocol. Extracted RNA was eluted from magnetic beads in 50 µl UltraPure DNase/RNase-free distilled water (Ambion CN 10977023). RNA concentration of eluted RNA was measured using Qubit RNA Broad Range (BR) assay kit (Fisher Scientific).

SARS-CoV-2 Inactivated Virus and Human Coronaviruses

In most experiments, fresh pooled saliva diluted 1:1 in TBE buffer (1× final concentration) were spiked with either gamma-irradiated (BEI cat #NR-52287, Lot no. 70033322) or heat-inactivated (BEI cat #NR-52286, Lot no. 70034991) SARS-CoV-2 virions. The reported genome copy number pre-inactivation for γ-irradiated and heat-inactivated SARS-CoV-2 are $1.7 \times 10^9$ and $3.75 \times 10^8$ genome equivalents/mL, respectively, for the specified lot numbers. The following reagent was deposited by the Centers for Disease Control and Prevention and obtained through BEI Resources, NIAID, NIH: SARS-Related Coronavirus 2, Isolate USA-WA1/2020, Gamma-irradiated, NR-52287, and heat-inactivated, NR-52286. Seasonal human coronaviruses (OC43 and 229E strains) were obtained from the World Reference Center for Emerging Viruses and Arboviruses at UTMB.

Genomic RNA for SARS-Related Coronavirus 2 (Isolate USA-WA1/2020), NR-52285, was obtained from BEI Resources. In addition, the 2019-nCoV_N_Positive Control (CN 10006625), SARS-CoV Control (CN 10006624), and MERS-CoV Control (CN 10006623) synthetic RNA transcripts were purchased from Integrated DNA Technologies. All virus stocks and RNA transcripts were aliquoted in small volumes and stored at −70° C. Stocks were serially diluted to the correct concentration in RNase-free water on the day of experimentation.

RT-qPCR Assay

We performed a multiplex RT-qPCR assay using the TaqPath RT-PCR COVID-19 kit (Thermo Fisher CN A47814) together with the TaqPath 1-step master mix—No ROX (Thermo Fisher CN A28523). To reduce cost, RT-qPCR reactions were prepared at half the suggested reaction mix volume (7.5 µL instead of 15 µL). 10 µL of either saliva in TBE buffer or extracted RNA were used as templates for the RT-qPCR reaction. All saliva samples used for pre-clinical studies were spiked with purified MS2 bacteriophage (1:40 MS2:sample) as an internal control prior to analysis by RT-qPCR. For clinical samples, MS2 was added to the preparation of the reaction mix (1 µL MS2 per reaction). COVID-19 positive control RNA at 25 genomic copies/µL was used. Negative control is UltraPure DNase/RNase-free distilled water (Ambion CN 10977023). All RT-qPCR reactions were performed in 0.2 mL 96-well reaction plates in a QuantStudio 3 system (Applied Biosciences).

For some experiments, samples were incubated in a hot water bath at 95° C. for 30 min. After cooling the sample on ice, 100 uL saliva was transferred to 96-deep-well plates pre-loaded with 100 uL of 2×TBE+1% Tween-20 buffer at 1:1 dilution ratio. 5 uL of this sample preparation was used as template for RT-qPCR reactions.

Multiplex RT-qPCR assay was performed using the TaqPath RT-PCR COVID-19 kit (Thermo Fisher CN A47814) together with the TaqPath 1-step master mix—No ROX (Thermo Fisher CN A28523). All RT-qPCR reactions, comprised of 5 uL template+5 uL of reaction mix (2.5 uL TaqPath 1-step master mix, 0.5 uL TaqPath primer/probe mix, 1.0 uL MS2, and 1.0 mase-free water), were performed in 384-well reaction plates in a QuantStudio 7 system (Applied Biosciences). The RT-qPCR was run using the standard mode, consisting of a hold stage at 25° C. for 2 min, 53° C. for 10 min, and 95° C. for 2 min, followed by 40 cycles of a PCR stage at 95° C. for 3 sec then 60° C. for 30 sec; with a 1.6° C./sec ramp up and ramp down rate.

The limit of detection (LoD) of the assay was performed by serial dilution of γ-irradiated SARS-CoV-2 ($0\text{-}5.0\times10^5$ viral copies/mL) used to spike pooled fresh saliva samples. LoD experiments were repeatedly performed at least five times in different machines.

In some experiments, the CDC-approved assay was used to validate our data using the TaqPath 1-step mix (Thermo Fisher CN A15300). Primers and probes targeting the N1, N2, and RP genes were purchased from Integrated DNA Technologies as listed: nCOV_N1 Forward Primer Aliquot (CN 10006830), nCOV_N1 Reverse Primer Aliquot (CN 10006831), nCOV_N1 Probe Aliquot (CN 10006832), nCOV_N2 Forward Primer Aliquot (CN 10006833), nCOV_N2 Reverse Primer Aliquot (CN 10006834), nCOV_N2 Probe Aliquot (CN 10006835), RNase P Forward Primer Aliquot (CN 10006836), RNase P Reverse Primer Aliquot (CN 10006837), RNase P Probe Aliquot (CN 10006838). The 2019-nCoV_N_Positive Control (IDT CN 10006625) was used as positive control at 50 copies/µL dilution. LoD experiments using CDC primers were performed at least three times.

Detergent Optimization

γ-irradiated SARS-CoV-2 ($1.0\times10^4$ viral copies/mL) was spiked into fresh human saliva (SARS-CoV-2 negative) and combined 1:1 with Tris-Borate-EDTA buffer (TBE) at a final working concentration of 1×.

Samples were treated with varying concentrations of detergents (Triton X-100 (Fisher Scientific), Tween 20 (Fisher Scientific), NP-40 (Fisher Scientific)) before or after heating at 95° C. for 30 min. All saliva samples were spiked with purified MS2 bacteriophage (1:40 MS2:sample) as an internal control prior to analysis by RT-qPCR (Fisher TaqPath COVID-19 Combo kit, QuantStudio 3).

Sample Volume Heat Treatment Optimization

γ-irradiated SARS-CoV-2 ($1.0\times10^4$ viral copies/mL; BEI) was spiked into fresh human saliva (SARS-CoV-2 negative) and combined 1:1 with Tris-Borate-EDTA buffer (TBE) at a final working concentration of 1×. The sample was distributed into either 50 mL conical (BD Falcon) or 1.5 mL microfuge tubes (Ambion), at either 10% (5 mL in 50 mL conical, 150 µL in 1.5 ml microfuge), 5% (2.5 ml in 50 mL conical, 75 µL in 1.5 mL microfuge), or 1% (0.5 mL in 50 mL conical, 15 µL in 1.5 mL microfuge) the vessel storage capacity. Samples were incubated in a hot water bath at 95° C. for 30 min. All saliva samples were spiked with purified MS2 bacteriophage (1:40 MS2:sample) as an internal control prior to analysis by RT-qPCR (Fisher TaqPath COVID-19 Combo kit, QuantStudio 3).

Sample Buffer Additive Optimization

γ-irradiated SARS-CoV-2 ($1.0\times10^4$ viral copies/mL) was spiked into fresh human saliva (SARS-CoV-2 negative) and combined 1:1 with Tris-Borate-EDTA buffer (TBE) at a final working concentration of 1× in 50 mL conical tubes (BD Falcon). Samples (1.0 mL in 50 mL conical tubes) were incubated in a hot water bath at 95° C. for 30 min. Following heat treatment, virus-spiked saliva was aliquoted in 1.5 mL tubes and combined with various RNA stabilizing agents to a final volume of 40 µL. Additives include RNaseI (1 U/µL), carrier RNA (0.05 µg/mL), glycogen (1 µg/µL), TCEP/EDTA (1×), Proteinase K (5 µg/µL), RNase-free BSA (1.25 mg/ml), RNAlater (1:1 ratio in place of TBE), or PBS-DTT (6.5 mM DTT in PBS, diluted 1:1 in place of TBE). All saliva samples were spiked with purified MS2 bacteriophage (1:40 MS2:sample) as an internal control prior to analysis by RT-qPCR (Fisher TaqPath COVID-19 Combo kit, QuantStudio 3).

Saliva Stability Optimization

Pre-aliquoted γ-irradiated SARS-CoV-2 ($1.0\times10^4$ viral copies/mL) was spiked into pre-aliquoted fresh human saliva (SARS-CoV-2 negative) and combined with Tris-Borate-EDTA buffer (TBE), at a final working concentration of 1×. Samples (0.5 mL in 50 mL conical tubes) were stored at 25° C. (ambient temperature), 4° C., −20° C., or −80° C. for 1, 2, 4, 8, 12, and 24 hours. All saliva samples were spiked with purified MS2 bacteriophage (1:40 MS2:sample) as an internal control prior to analysis by RT-qPCR (Fisher TaqPath COVID-19 Combo kit, QuantStudio 3).

Data Analysis

Following completion of RT-qPCR, data were processed using QuantStudio Design and Analysis Software (version 2.4). Cycle threshold (Ct) values were plotted as single replicate values on a scatter plot, using GraphPad Prism 8 (version 8.4.2). Sensitivity, specificity, false positive, false negative, positive predictive values, and negative predictive values were calculated using the current standard for SARS-CoV-2 detection (NP swabs in VTM with RNA extraction) as confirmation of true disease positive and disease negative status.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method of detecting viral polynucleotides in a saliva sample comprising:
   combining the saliva sample with Tris Borate Ethylenediaminetetraacetic acid (TBE) at about a 1:3 w/w to about 3:1 w/w ratio prior to heating the saliva sample, to form a mixture;
   heating the mixture at about 95 degrees Celsius for about 15 minutes to about 30 minutes;
   after heating, contacting the heated mixture with one or more non-ionic detergents, wherein the one or more non-ionic detergents are present in a final concentration of about 0.25% to about 1% by weight to provide a test sample; and
   subjecting the test sample to conditions that amplify target viral polynucleotides in the test sample using RT-qPCR, and detecting the viral polynucleotides in the biological sample.

2. The method of claim 1 wherein the viral polynucleotides are SARS-CoV-2 polynucleotides or a variant thereof.

3. The method of claim 2 wherein the target viral polynucleotides comprise one or more of ORF1ab, N1-gene, N2-gene, and S-gene.

4. A method of detecting polynucleotides from SARS-CoV-2 in a saliva sample comprising:
   mixing the saliva sample with Tris Borate Ethylenediaminetetraacetic acid (TBE) in a 1:1 ratio prior to heating the saliva sample, to form a mixture;
   heating the mixture at about 95 degrees Celsius for about 15-30 minutes;
   after heating, contacting the mixture with polysorbate 20, wherein the polysorbate 20 is present in a final concentration of 0.5% or less by weight to provide a test sample; and
   subjecting the test sample to conditions that amplify target polynucleotides of SARS-CoV-2 in the test sample using RT-qPCR, wherein the target polynucleotides comprise at least a portion of one or more of ORF1ab, N1-gene, N2-gene, and S-gene, and detecting the polynucleotides from SARS-CoV-2 in the saliva sample.

* * * * *